(12) United States Patent
Braden et al.

(10) Patent No.: US 11,167,257 B2
(45) Date of Patent: Nov. 9, 2021

(54) SURFACTANT COMPOSITIONS AND USE THEREOF AS INVERTER OF WATER-IN-OIL EMULSION POLYMERS

(71) Applicant: Ecolab USA Inc., St. Paul, MN (US)

(72) Inventors: Michael L. Braden, Sugar Land, TX (US); Ashish Dhawan, Aurora, IL (US); Wesley L. Whipple, Naperville, IL (US); Pious Kurian, Sugar Land, TX (US)

(73) Assignee: Ecolab USA Inc., St. Paul, MN (US)

( * ) Notice: Subject to any disclaimer, the term of this patent is extended or adjusted under 35 U.S.C. 154(b) by 210 days.

(21) Appl. No.: 16/228,150

(22) Filed: Dec. 20, 2018

(65) Prior Publication Data

US 2019/0201858 A1 Jul. 4, 2019

Related U.S. Application Data

(60) Provisional application No. 62/611,264, filed on Dec. 28, 2017.

(51) Int. Cl.
  *B01F 17/00* (2006.01)
  *C07C 43/23* (2006.01)
  (Continued)

(52) U.S. Cl.
  CPC ...... *B01F 17/0021* (2013.01); *B01F 17/0028* (2013.01); *B01F 17/0085* (2013.01); *C02F 1/547* (2013.01); *C02F 1/56* (2013.01); *C07C 43/23* (2013.01); *C08G 65/2612* (2013.01); *C08J 3/095* (2013.01); *C08K 5/13* (2013.01); *C08L 71/02* (2013.01); *C09K 8/36* (2013.01);
  (Continued)

(58) Field of Classification Search
  None
  See application file for complete search history.

(56) References Cited

U.S. PATENT DOCUMENTS 3,350,353 A 10/1967 Alvey
3,624,019 A 11/1971 Anderson et al.
(Continued)

FOREIGN PATENT DOCUMENTS

EP 0 097 567 A2 1/1984
EP 0 202 780 A2 11/1986
(Continued)

OTHER PUBLICATIONS

Al-Sabagh, Ahmed M. et al., Investigation of Kinetic and Rheological Properties for the Demulsification Process, Egyptian Journal of Petroleum (2013) 22, pp. 117-127.
(Continued)

*Primary Examiner* — John J Figueroa
(74) *Attorney, Agent, or Firm* — Stinson LLP

(57) ABSTRACT

Surfactants capable of releasing and/or dissolving polymers to form water-soluble or water-dispersible polymer solutions are disclosed. In addition, polymer compositions containing a water-in-oil emulsion comprising the surfactant are provided and can be used, for example, in methods of dissolving a polymer. These surfactants and polymer compositions can be used in various industries including for water clarification, papermaking, sewage and industrial water treatment, drilling mud stabilizers, and enhanced oil recovery.

20 Claims, 16 Drawing Sheets

(51) Int. Cl.
*C08G 65/26* (2006.01)
*C11D 1/72* (2006.01)
*C09K 8/36* (2006.01)
*C09K 8/584* (2006.01)
*C09K 8/588* (2006.01)
*C08L 71/02* (2006.01)
*C02F 1/54* (2006.01)
*C02F 1/56* (2006.01)
*C08J 3/09* (2006.01)
*C08K 5/13* (2006.01)
*D21H 21/50* (2006.01)

(52) U.S. Cl.
CPC .............. *C09K 8/584* (2013.01); *C09K 8/588* (2013.01); *C11D 1/72* (2013.01); *D21H 21/50* (2013.01)

(56) References Cited

U.S. PATENT DOCUMENTS

| | | | |
|---|---|---|---|
| 3,734,873 A | 5/1973 | Anderson et al. | |
| 3,947,425 A | 3/1976 | Freeman et al. | |
| 4,136,045 A | 1/1979 | Gault et al. | |
| 4,211,862 A | 7/1980 | Pechhold et al. | |
| 4,260,437 A | 4/1981 | Nakagawa et al. | |
| 4,378,453 A | 3/1983 | Yotsumoto et al. | |
| 4,506,051 A * | 3/1985 | Rance | C08J 3/02 524/233 |
| 4,525,496 A * | 6/1985 | Adaway | C09K 8/584 523/337 |
| 4,537,701 A | 8/1985 | Oppenlaender et al. | |
| 4,575,521 A | 3/1986 | Cote et al. | |
| 4,649,102 A | 3/1987 | Mukunoki et al. | |
| 4,737,265 A | 4/1988 | Merchant, Jr. et al. | |
| 4,848,442 A | 7/1989 | Iyer et al. | |
| 4,918,123 A | 4/1990 | Yang et al. | |
| 5,021,498 A | 6/1991 | Stephenson et al. | |
| 5,073,248 A | 12/1991 | Stephenson et al. | |
| 5,207,954 A | 5/1993 | Lewis et al. | |
| 5,314,955 A | 5/1994 | Halladay | |
| 5,362,615 A | 11/1994 | Hagemann et al. | |
| 5,779,632 A | 7/1998 | Dietz et al. | |
| 5,789,472 A | 8/1998 | Ryan et al. | |
| 5,945,494 A | 8/1999 | Neff et al. | |
| 5,961,840 A | 10/1999 | Ryles et al. | |
| 5,973,064 A | 10/1999 | Zhao et al. | |
| 5,981,622 A | 11/1999 | Geoffrey | |
| 5,998,530 A | 12/1999 | Krull et al. | |
| 6,102,999 A | 8/2000 | Cobb, III et al. | |
| 6,120,678 A | 9/2000 | Stephenson et al. | |
| 6,268,406 B1 * | 7/2001 | Chatterji | C04B 24/163 166/250.14 |
| 6,294,093 B1 | 9/2001 | Selvarajan et al. | |
| 6,313,367 B1 | 11/2001 | Breen | |
| 6,316,583 B1 | 11/2001 | Gerber | |
| 6,369,182 B1 | 4/2002 | Whipple et al. | |
| 6,465,528 B1 | 10/2002 | Holtrup et al. | |
| 6,908,962 B1 | 6/2005 | Frankenbach et al. | |
| 7,429,625 B2 | 9/2008 | Harrington et al. | |
| 7,951,857 B2 | 5/2011 | Crews et al. | |
| 8,840,820 B2 | 9/2014 | Yancey et al. | |
| 9,034,093 B2 | 5/2015 | Stark et al. | |
| 9,464,193 B2 | 10/2016 | Hagiopol et al. | |
| 2004/0063597 A1 | 4/2004 | Adair et al. | |
| 2005/0098759 A1 | 5/2005 | Frankenbach et al. | |
| 2006/0111508 A1 | 5/2006 | Dailey, Jr. | |
| 2007/0062102 A1 | 3/2007 | Krull et al. | |
| 2007/0221539 A1 * | 9/2007 | Cohrs | C10L 10/18 208/18 |
| 2009/0312476 A1 | 12/2009 | Korth et al. | |
| 2010/0151396 A1 | 6/2010 | Papachristos et al. | |
| 2010/0204351 A1 | 8/2010 | Swedo et al. | |
| 2014/0051620 A1 * | 2/2014 | Soane | C09K 8/36 508/471 |
| 2014/0190692 A1 | 7/2014 | Hibbeler et al. | |
| 2015/0150255 A1 | 6/2015 | Lapitsky et al. | |
| 2015/0291494 A1 | 10/2015 | Huc et al. | |
| 2015/0307788 A1 | 10/2015 | McDaniel et al. | |
| 2015/0367307 A1 | 12/2015 | Shen et al. | |
| 2016/0017203 A1 * | 1/2016 | Frederick | C09K 8/64 166/308.3 |
| 2016/0333252 A1 | 11/2016 | Brinkman et al. | |
| 2016/0361699 A1 * | 12/2016 | Floyd, III | B01F 17/005 |
| 2017/0037300 A1 | 2/2017 | Li et al. | |

FOREIGN PATENT DOCUMENTS

| | | |
|---|---|---|
| EP | 0 222 587 A1 | 5/1987 |
| EP | 0 261 679 A2 | 3/1988 |
| EP | 0 374 458 A2 | 6/1990 |
| GB | 1029501 | 5/1966 |
| GB | 1115611 | 5/1968 |
| GB | 2146260 A | 4/1985 |
| WO | 2009/013536 A2 | 1/2009 |
| WO | 2013/112503 A1 | 8/2013 |
| WO | 2017/120455 A1 | 7/2017 |

OTHER PUBLICATIONS

Downs, H. H. et al., Enhanced Oil Recovery by Wettability Alteration, Chapter 32 (1989) American Chemical Society, 19 pages.
Hauck, G. et al., Influence of Additives and Surface Topography on the Alignment of Nematic Liquid Crystals, Crystal Res. & Technol. 17 (7) (1982), pp. 865-869.
International Search Report and Written Opinion dated Mar. 13, 2019 relating to PCT Patent Application No. PCT/US2018/066760, 14 pages.
International Search Report and Written Opinion dated Mar. 28, 2019 relating to PCT Patent Application No. PCT/US2018/066785, 12 pages.

* cited by examiner

SURFACTANT COMPOSITIONS AND USE THEREOF AS INVERTER OF WATER-IN-OIL EMULSION POLYMERS

CROSS REFERENCE TO RELATED APPLICATIONS

This application claims priority to U.S. Provisional Patent Application Ser. No. 62/611,264 filed on Dec. 28, 2017, the disclosure of which is incorporated herein by reference in its entirety.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

Surfactants capable of releasing and/or dissolving polymers to form water-soluble or water-dispersible polymer solutions are disclosed. In addition, polymer compositions containing a water-in-oil emulsion comprising the surfactant are provided and can be used, for example, in methods of dissolving a polymer. These surfactants and polymer compositions can be used in various industries including for water clarification, papermaking, sewage and industrial water treatment, drilling mud stabilizers, and enhanced oil recovery.

BACKGROUND OF THE INVENTION

Various synthetic and naturally-occurring water-soluble or water-dispersible polymers can be used in a variety of commercial applications. These polymers are commercially available as powders, finely-divided solids, or water-in-oil emulsion polymers that require the polymer to be dissolved in water. While the polymers are water-soluble or water-dispersible, it can be difficult to prepare solutions or homogeneous dispersions because of slow dissolution or slow dispersion into the water. Further, polymers can clump or remain as agglomerates on contact with water. Although these clumps eventually dissolve or disperse using agitation, it can be impractical to agitate the solution for a sufficiently long time to obtain complete dissolution of the polymer particles.

Additionally, surfactants, and compositions thereof, can invert and/or activate water-in-oil emulsion polymers to aid the dissolution and dispersion of those polymers. Such inversion surfactants can be used to increase the dissolution of various emulsion polymers so the time for dissolution and degree of dissolution of the polymer is increased.

To reduce the time needed for polymer solids or inverse emulsion polymers to dissolve or disperse in aqueous solution, an inversion surfactant can be used.

Ethoxylated alkylphenols and alkylphenol-formaldehyde resins, particularly containing nonylphenol moiety as one of the building blocks have been used in the industry as one class of inversion surfactants. However, nonylphenols and their ethoxylated derivatives are known to be toxic, specifically as endocrine-hormone disrupters. Thus, there is a need to replace these chemistries with nonylphenol-free alternatives that are more environmentally friendly.

Because of the toxicity of nonylphenols and their ethoxylated derivatives, industrial use has largely shifted to linear/branched alcohol ethoxylates (LAEs). However, LAEs are generally not as effective as nonylphenol ethoxylates. Therefore, a need exists for novel inversion surfactants that are effective for dissolving or dispersing water-soluble or water-dispersible polymers in several industries.

BRIEF SUMMARY OF THE INVENTION

A polymer composition is provided that includes a water-in-oil emulsion containing an aqueous phase including water and a water-soluble or water-dispersible polymer, and an oil phase including an oil and an emulsifying agent; and an inversion surfactant having the structure of Formula 1:

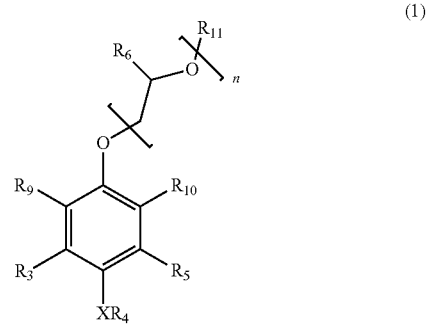

(1)

wherein $R_3$, $R_5$, $R_9$, and $R_{10}$ are independently hydrogen or $C_1$-$C_{22}$ alkyl; $R_4$ is $C_4$-$C_{30}$ alkyl; $R_6$ is H, alkyl, or aryl; $R_{11}$ is hydrogen, alkyl, alkylaryl, or aryl; X is —O— or —$NR_8$; $R_8$ is hydrogen or $C_1$-$C_4$ alkyl; and n is an integer from 1 to 20.

A polymer composition is also provided that includes a water-in-oil emulsion including an aqueous phase containing water and a water-soluble or water-dispersible polymer, an oil phase containing an oil and an emulsifying agent, and an inversion surfactant having the structure of Formula 1:

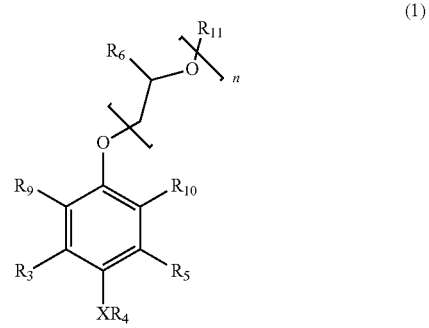

(1)

wherein $R_3$, $R_5$, $R_9$, and $R_{10}$ are independently hydrogen or $C_1$-$C_{22}$ alkyl; $R_4$ is $C_4$-$C_{30}$ alkyl; $R_6$ is H, alkyl, or aryl; $R_{11}$ is hydrogen, alkyl, alkylaryl, or aryl; X is —O— or —$NR_8$; $R_8$ is hydrogen or $C_1$-$C_4$ alkyl; and n is an integer from 1 to 20.

A polymer composition is further provided that includes a water-in-oil emulsion containing an aqueous phase including water and a water-soluble or water-dispersible polymer, and an oil phase containing an oil and an emulsifying agent; and an aqueous solution containing an inversion surfactant having the structure of Formula 1.

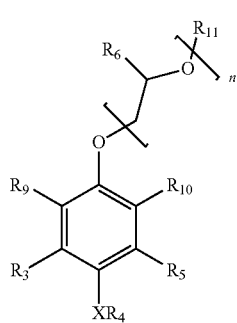

(1)

wherein $R_3$, $R_5$, $R_9$, and $R_{10}$ are independently hydrogen or $C_1$-$C_{22}$ alkyl; $R_4$ is $C_4$-$C_{30}$ alkyl; $R_6$ is H, alkyl, or aryl; $R_{11}$ is hydrogen, alkyl, alkylaryl, or aryl; X is —O— or —$NR_8$; $R_8$ is hydrogen or $C_1$-$C_4$ alkyl; and n is an integer from 1 to 20.

A polymer composition is also provided that comprises a water-soluble or water-dispersible polymer, an oil, a suspending agent, and a surfactant having the structure of Formula 1:

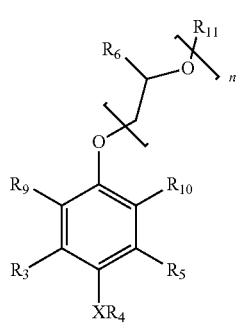

(1)

wherein $R_3$, $R_5$, $R_9$, and $R_{10}$ are independently hydrogen or $C_1$-$C_{22}$ alkyl; $R_4$ is $C_4$-$C_{30}$ alkyl; $R_6$ is H, alkyl, or aryl; X is —O— or —$NR_8$; $R_8$ is hydrogen or $C_1$-$C_4$ alkyl; $R_{11}$ is hydrogen, alkyl, alkylaryl, or aryl; and n is an integer from 1 to 20.

Preferably, for the polymer composition described herein, in the inversion surfactant having the structure of Formula 1, X is —O—.

Further, for the inversion surfactant having the structure of Formula 1, n can be an integer from 2 to 20. Preferably, n is an integer from 4 to 16. More preferably, n is an integer from 4 to 10.

For the inversion surfactant having the structure of Formula 1, $R_4$ can be $C_4$-$C_{16}$ alkyl; $R_4$ can also be $C_4$-$C_{12}$ alkyl; preferably, $R_4$ is $C_8$-$C_{12}$ alkyl; and more preferably, $R_4$ is octyl.

In the inversion surfactant having the structure of Formula 1, $R_3$, $R_5$, $R_9$, and $R_{10}$ can independently be hydrogen or methyl, and preferably, $R_3$, $R_5$, $R_9$, and $R_{10}$ are hydrogen.

Additionally, $R_6$ can be hydrogen, methyl, butyl, or benzyl, or a combination thereof. For example, $R_6$ can be methyl, hydrogen, or a combination thereof. Preferably, $R_6$ can be hydrogen.

For the structure of Formula 1, $R_{11}$ can be hydrogen or alkyl; preferably, hydrogen or methyl; most preferably, hydrogen.

In the described polymer composition, the inversion surfactant having the structure of Formula 1 can have a concentration of from about 0.1 wt. % to about 10 wt. % based on the total weight of the polymer composition. Preferably, the inversion surfactant having the structure of Formula 1 has a concentration of from about 0.5 wt. % to about 5 wt. % based on the total weight of the polymer composition.

The polymer composition can comprise from about 5 wt. % to about 70 wt. %, of the water-soluble or water-dispersible polymer. Preferably, the polymer composition comprises from about 18 wt. % to about 65 wt. % of the water-soluble or water-dispersible polymer.

A method of dissolving the water-soluble or water-dispersible polymer of the polymer composition is also provided, the method comprising contacting the water-in-oil emulsion with the inversion surfactant having the structure of Formula 1.

A further method of dissolving the water-soluble or water-dispersible polymer of the polymer composition is also provided, the method comprising contacting the water-in-oil emulsion further comprising the inversion surfactant having the structure of Formula 1 with an aqueous solution.

Another method of dissolving the water-soluble or water-dispersible polymer of the polymer composition is provided, the method comprising contacting the water-in-oil emulsion with an aqueous solution comprising the inversion surfactant having the structure of Formula 1.

The polymer composition or methods described herein can have the polymer composition further comprise an ethoxylated $C_{10}$-$C_{16}$ alcohol; a $C_{12}$-$C_{13}$ primary alcohol of linear and mono-methyl branched alcohol having on average 9 moles ethylene oxide; an ethoxylate of a saturated $C_{12\text{-}15}$ alcohol; an ethoxylated $C_{12\text{-}14}$ alcohol; an ethoxylated primary branched saturated $C_{13}$ alcohol; an ethoxylated $C_{10}$ Guerbet alcohol; an ethoxylated saturated iso-$C_{13}$ alcohol; a saturated, predominantly unbranched $C_{13\text{-}15}$ oxo alcohol having 11 ethylene oxide groups; a secondary alcohol ethoxylate; a nonionic, alkoxylated alcohol; a polyoxyethylene (9) synthetic primary $C_{13}/C_{15}$ alcohol; an isotridecyl alcohol ethoxylated with an average of 9 moles ethylene oxide; an ethoxylated linear primary $C_{12\text{-}14}$ alcohol; an ethoxylated nonylphenol; tert-octylphenoxypoly(ethoxyethanol); a tridecyl ether phosphate; a polyoxyethylene (5) soyaallylamine; a polyethylene glycol (PEG) 400 monooleate; a PEG 600 monooleate; aPEG-25 castor oil; a PEG-30 castor oil; a PEG-40 castor oil; an aliphatic phosphate ester with 10 moles EO; an aliphatic phosphate ester with 6 moles EO; an oleic acid monoethanol amide with 14 moles ethylene oxide; a soyamine ethoxylate; or a combination thereof.

The methods described herein can have the inversion surfactant be activated by contacting the inversion surfactant with an inversion aid.

For the methods described herein, the inversion aid can comprise glycol, a polypropylene glycol, polyglycerol, urea, sorbitol, sucrose, glycerol, a polyglycerol, a phosphate, choline chlorine, guanidine, dioctyl-sulfosuccinate, malic acid, lactic acid, N-(phosphonomethyl)glycine, 2-phosphonopropanoic acid, 3-phosphonopropanoic acid, 4-phosphonobutanoic acid, a phosphinosuccinic oligomer, or a combination thereof.

The inversion surfactant can be activated by contacting the inversion surfactant with an aqueous solution. Further, the aqueous solution can contain a salt.

The inversion surfactant can be activated by increasing the temperature of the aqueous solution, and preferably, the temperature of the aqueous solution is increased from about 10° C. to about 65° C.

A compound is also provided that has the structure of Formula 2:

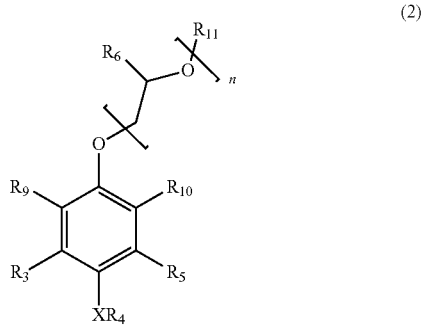

(2)

wherein $R_3$, $R_5$, $R_9$, and $R_{10}$ are independently hydrogen or $C_1$-$C_{22}$ alkyl; $R_4$ is $C_4$-$C_{30}$ branched alkyl; $R_6$ is H, alkyl, or aryl; Ru is hydrogen, alkyl, alkylaryl, or aryl; X is —O— or —$NR_8$; $R_8$ is hydrogen or $C_1$-$C_4$ alkyl; and n is an integer from 1 to 20.

Preferably, the compound having the structure of formula 2 has $R_3$, $R_5$, $R_9$, and $R_{10}$ are hydrogen; $R_4$ is $C_8$-$C_{16}$ branched alkyl; $R_6$ and $R_{11}$ are hydrogen; X is —O—; and n is an integer from 1 to 20.

Other objects and features will be in part apparent and in part pointed out hereinafter.

BRIEF DESCRIPTION OF THE SEVERAL VIEWS OF THE DRAWING

Corresponding reference characters indicate corresponding parts throughout the drawings.

DETAILED DESCRIPTION OF THE INVENTION

Figure 1:
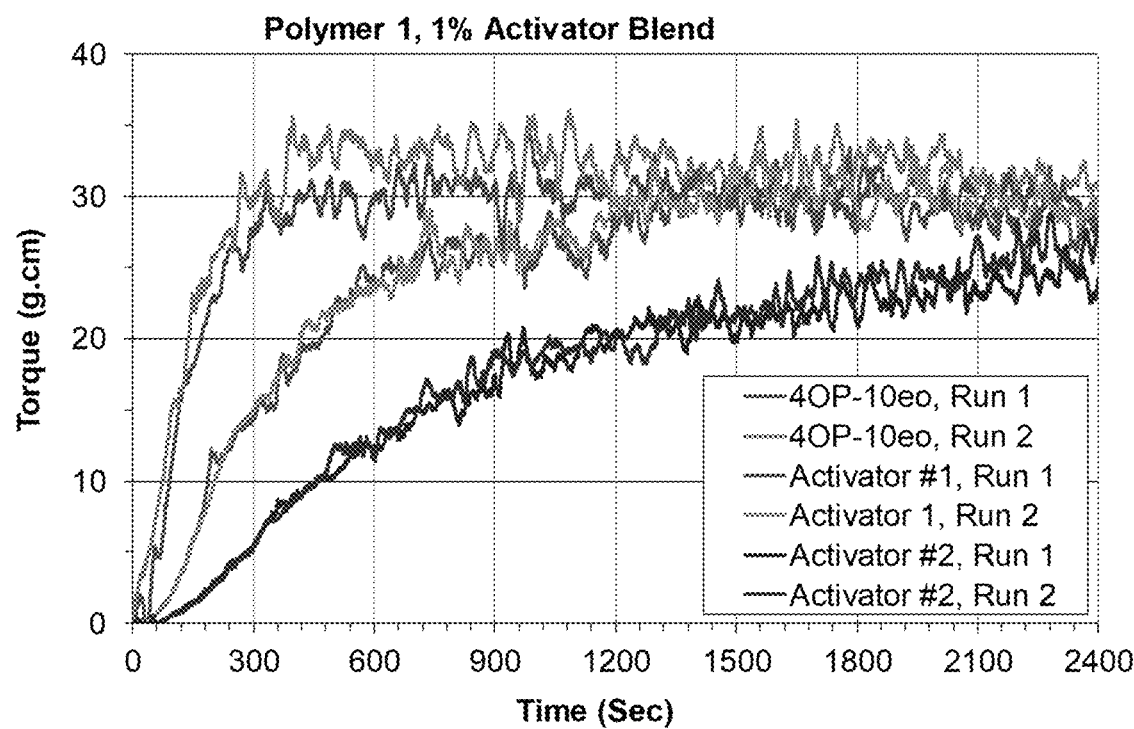
FIG. 1 is a graph of the torque versus time and shows the inversion torque profile (0.5% invert) for polymer 1 with approximately 1% activating surfactant.

Inversion surfactants are provided that can dissolve water-soluble or water-dispersible polymers rapidly and completely in aqueous solution. The polymer compositions containing the surfactants described herein can be used in various industries including for water clarification, papermaking, sewage and industrial water treatment, drilling mud stabilizers, and enhanced oil recovery.

Polymer compositions including water-in-oil emulsions and inversion surfactants are provided. Also, methods of dissolving a water-soluble or water-dispersible polymer are disclosed.

Therefore, polymer compositions and methods using the polymer compositions are described herein. The polymer composition comprises a water-in-oil emulsion comprising an aqueous phase comprising water and a water-soluble or water-dispersible polymer, and an oil phase comprising an oil and an emulsifying agent; and an inversion surfactant having the structure of Formula 1:

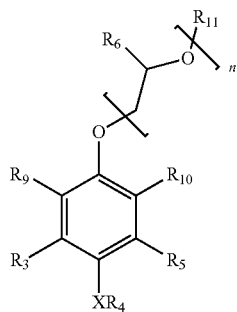
(1)

wherein $R_3$, $R_5$, $R_9$, and $R_{10}$ are independently hydrogen or $C_1$-$C_{22}$ alkyl; $R_4$ is $C_4$-$C_{22}$ alkyl; $R_6$ is H, alkyl, or aryl; $R_{11}$ is hydrogen, alkyl, alkylaryl, or aryl; X is —O— or —NR$_8$; $R_8$ is hydrogen or $C_1$-$C_4$ alkyl; and n is an integer from 1 to 20.

A polymer composition is also provided that includes a water-in-oil emulsion containing an aqueous phase comprising water and a water-soluble or water-dispersible polymer, an oil phase comprising an oil and an emulsifying agent, and an inversion surfactant having the structure of Formula 1:

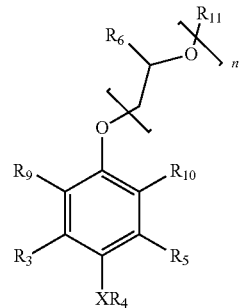
(1)

wherein $R_3$, $R_5$, $R_9$, and $R_{10}$ are independently hydrogen or $C_1$-$C_{22}$ alkyl; $R_4$ is $C_4$-$C_{30}$ alkyl; $R_6$ is H, alkyl, or aryl; $R_{11}$ is hydrogen, alkyl, alkylaryl, or aryl; X is —O— or —NR$_8$; $R_8$ is hydrogen or $C_1$-$C_4$ alkyl; and n is an integer from 1 to 20.

A polymer composition is further provided that includes a water-in-oil emulsion containing an aqueous phase comprising water and a water-soluble or water-dispersible polymer, and an oil phase comprising an oil and an emulsifying agent; and an aqueous solution containing an inversion surfactant having the structure of Formula 1.

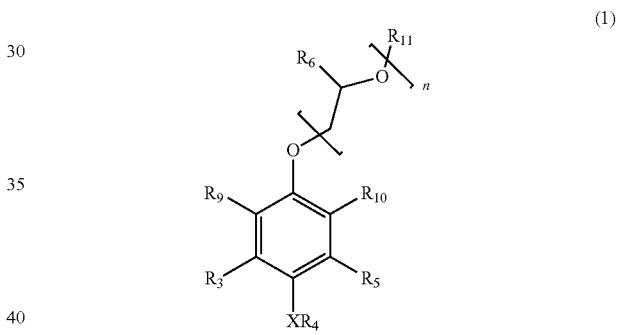
(1)

wherein $R_3$, $R_5$, $R_9$, and $R_{10}$ are independently hydrogen or $C_1$-$C_{22}$ alkyl; $R_4$ is $C_4$-$C_{30}$ alkyl; $R_6$ is H, alkyl, or aryl; $R_{11}$ is hydrogen, alkyl, alkylaryl, or aryl; X is —O— or —NR$_8$; $R_8$ is hydrogen or $C_1$-$C_4$ alkyl; and n is an integer from 1 to 20.

A polymer composition is also provided that comprises a water-soluble or water-dispersible polymer, an oil, a suspending agent, and a surfactant having the structure of Formula 1:

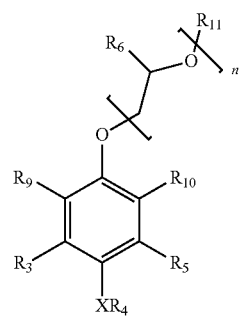
(1)

wherein $R_3$, $R_5$, $R_9$, and $R_{10}$ are independently hydrogen or $C_1$-$C_{22}$ alkyl; $R_4$ is $C_4$-$C_{30}$ alkyl; $R_6$ is H, alkyl, or aryl; X is —O— or —NR$_8$; $R_8$ is hydrogen or $C_1$-$C_4$ alkyl; $R_{11}$ is hydrogen, alkyl, alkylaryl, or aryl; and n is an integer from 1 to 20.

A compound is also provided that has the structure of Formula 2:

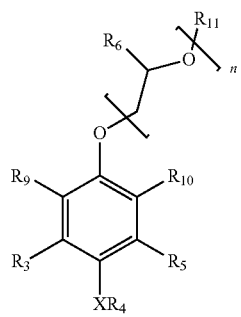

(2)

wherein $R_3$, $R_5$, $R_9$, and $R_{10}$ are independently hydrogen or $C_1$-$C_{22}$ alkyl; $R_4$ is $C_4$-$C_{30}$ branched alkyl; $R_6$ is H, alkyl, or aryl; $R_{11}$ is hydrogen, alkyl, alkylaryl, or aryl; X is —O— or —NR$_8$; $R_8$ is hydrogen or $C_1$-$C_4$ alkyl; and n is an integer from 1 to 20.

Preferably, the compound having the structure of formula 2 has $R_3$, $R_5$, $R_9$, and $R_{10}$ are hydrogen; $R_4$ is $C_8$-$C_{16}$ branched alkyl; $R_6$ and $R_{11}$ are hydrogen; X is —O—; and n is an integer from 1 to 20.

Preferably, in the inversion surfactant of Formula 1 or 2, X is —O—.

Further, in the inversion surfactant of Formula 1 or 2, n can be an integer from 2 to 20. Preferably, n is an integer from 4 to 16. More preferably, n is an integer from 4 to 10.

For the inversion surfactant of Formula 1, $R_4$ can be $C_4$-$C_{16}$ alkyl; $R_4$ can also be $C_4$-$C_{12}$ alkyl; preferably, $R_4$ is $C_8$-$C_{12}$ alkyl; and more preferably, $R_4$ is octyl.

In the inversion surfactant of Formula 1 or 2, $R_3$, $R_5$, $R_9$, and $R_{10}$ can independently be hydrogen or methyl. Preferably, $R_3$, $R_5$, $R_9$, and $R_{10}$ are hydrogen.

Additionally, for the inversion surfactant of Formula 1 or 2, $R_6$ can be hydrogen, methyl, butyl, or benzyl. For example, $R_6$ can be methyl. Alternatively, $R_6$ can be hydrogen.

For the inversion surfactant of Formula 1 or 2, $R_{11}$ can be hydrogen or alkyl; preferably, hydrogen or methyl; most preferably, hydrogen.

The polymer composition can comprise from about 5 wt. % to about 70 wt. %, from about 10 wt. % to about 70 wt. %, from about 20 wt. % to about 70 wt. %, from about 30 wt. % to about 70 wt. %, from about 40 wt. % to about 70 wt. %, from about 50 wt. % to about 70 wt. %, from about 60 wt. % to about 70 wt. %, from about 10 wt. % to about 60 wt. %, from about 10 wt. % to about 50 wt. %, from about 15 wt. % to about 70 wt. %, from about 15 wt. % to about 65 wt. %, from about 18 wt. % to about 65 wt. %, from about 20 wt. % to about 60 wt. %, from about 20 wt. % to about 50 wt. %, from about 25 wt. % to about 70 wt. %, from about 25 wt. % to about 60 wt. %, from about 25 wt. % to about 50 wt. %, of the water-soluble or water-dispersible polymer. Preferably, the polymer composition comprises from about 18 wt. % to about 65 wt. % of the water-soluble or water-dispersible polymer.

The polymer composition can be a slurry comprising a water-soluble polymer suspended in an oil-based vehicle with a suspension agent and a surfactant of Formula 1 or 2. The approximate size of the water-soluble polymer is preferably 75-200 mesh.

Specifically, the oil-based vehicle can be petroleum distillate. Petroleum distillates are products distilled from petroleum crude oil and use different CAS # identifiers depending upon the molecular weight distribution and processing technology used. A petroleum distillate suitable for the present composition can be, for example, CAS #64742-47-8.

The suspension aid can be a variation of diblock copolymers based on styrene and ethylene/propylene. The composition can also contain a dispersant such as organophilic clay or a synthetic alternative as the suspension agent.

The inversion surfactant having the structure of Formula 1 or 2 can be blended with another inversion surfactants. For example, the other inversion surfactants of interest include those listed in the following table and combinations thereof.

| Trade Name | Chemistry | Trade Name |
| --- | --- | --- |
| Alfonic 1412-7 | Ethoxylated $C_{10}$-$C_{16}$ alcohols | Alfonic 1412-7 |
| Novel 23E9 | $C_{12}$-$C_{13}$ primary alcohol of linear and mono-methyl branched alcohols having on average 9 moles EO | Novel 23E9 |
| Synperonic A11 | Ethoxylate of a saturated $C_{12-15}$ alcohol | Synperonic A11 |
| Surfonic 1412-12 | Ethoxylated $C_{12-14}$ alcohol | Surfonic 1412-12 |
| Synperonic 13/7 | Ethoxylated primary branched saturated $C_{13}$ alcohol | Synperonic 13/7 |
| Lutensol TO10 | Ethoxylated $C_{10}$ Guerbet alcohol | Lutensol TO10 |
| Lutensol TO12 | Ethoxylated saturated iso-$C_{13}$ alcohol | Lutensol TO12 |
| Lutensol AO11 | Saturated, predominantly unbranched $C_{13-15}$ oxo alcohols having 11 EO groups | Lutensol AO11 |
| Tergitol 15-S-9 | Secondary Alcohol Ethoxylate | Tergitol 15-S-9 |
| Tergitol 15-S-12 | Secondary Alcohol Ethoxylate | Tergitol 15-S-12 |
| Plurafac RA 20 | Nonionic, alkoxylated alcohol | Plurafac RA 20 |
| Plurafac RA 30 | Nonionic, alkoxylated alcohol | Plurafac RA 30 |
| Synperonic A9 | Polyoxyethylene (9) synthetic primary $C_{13}$/$C_{15}$ alcohol | Synperonic A9 |
| Alfonic TDA9 | Isotridecyl alcohol ethoxylated with an average of 9 moles EO | Alfonic TDA9 |
| Novel 1412-11 | Ethoxylated linear primary $C_{12-14}$ alcohol | Novel 1412-11 |
| Tergitol NP-9.5 | Ethoxylated nonylphenol | Tergitol NP-9.5 |
| Tergitol NP-10.5 | Ethoxylated nonylphenol | Tergitol NP-10.5 |
| Triton X-114 | tert-octylphenoxypoly(ethoxyethanol) | Triton X-114 |
| Rhodafac RS-410 | Tridecyl ether phosphate | Rhodafac RS-410 |
| Ethomeen S/15 | Polyoxyethylene (5) soyaallylamines | Ethomeen S/15 |
| Ethox MO-9 | PEG 400 monooleate | Ethox MO-9 |
| Ethox MO-14 | PEG 600 monooleate | Ethox MO-14 |
| Ethox CO-25 | PEG-25 Castor oil | Ethox CO-25 |
| Alkamul EL-620 | PEG-30 Castor oil | Alkamul EL-620 |
| Ethox CO-40 | PEG-40 Castor oil | Ethox CO-40 |
| Rhodafac RS-710 | Aliphatic phosphate ester, 10 moles EO | Rhodafac RS-710 |
| Rhodafac RS-610 | Aliphatic phosphate ester, 6 moles EO | Rhodafac RS-610 |

-continued

| Trade Name | Chemistry | Trade Name |
|---|---|---|
| Serdox NXC-14 | Oleic acid monoethanol amide + 14 EO | Serdox NXC-14 |
| Ethomeen S/25 | Soyamine ethoxylate | Ethomeen S/25 |

The inversion surfactant having the structure of Formula 1 or 2 can be blended with an ethoxylated $C_{10}$-$C_{16}$ alcohol; a $C_{12}$-$C_{13}$ primary alcohol of linear and mono-methyl branched alcohol having on average 9 moles ethylene oxide; an ethoxylate of a saturated $C_{12\text{-}15}$ alcohol; an ethoxylated $C_{12\text{-}14}$ alcohol; an ethoxylated primary branched saturated $C_{13}$ alcohol; an ethoxylated $C_{10}$ Guerbet alcohol; an ethoxylated saturated iso-$C_{13}$ alcohol; a saturated, predominantly unbranched $C_{13\text{-}15}$ oxo alcohol having 11 ethylene oxide groups; a secondary alcohol ethoxylate; a nonionic, alkoxylated alcohol; a polyoxyethylene (9) synthetic primary $C_{13}$/$C_{15}$ alcohol; an isotridecyl alcohol ethoxylated with an average of 9 moles ethylene oxide; an ethoxylated linear primary $C_{12\text{-}14}$ alcohol; an ethoxylated nonylphenol; tert-octylphenoxypoly(ethoxyethanol); a tridecyl ether phosphate; a polyoxyethylene (5) soyaallylamine; a polyethylene glycol (PEG) 400 monooleate; a PEG 600 monooleate; aPEG-25 castor oil; a PEG-30 castor oil; a PEG-40 castor oil; an aliphatic phosphate ester with 10 moles EO; an aliphatic phosphate ester with 6 moles EO; an oleic acid monoethanol amide with 14 moles ethylene oxide; a soyamine ethoxylate; or a combination thereof.

The methods described herein, wherein the inversion surfactant is activated by contacting the inversion surfactant with an inversion aid.

The methods described herein, wherein the inversion aid comprises glycol, a polyethylene glycol, a polypropylene glycol, polyglycerol, urea, sorbitol, sucrose, glycerol, a phosphate, choline chlorine, guanidine, dioctyl-sulfosuccinate, malic acid, lactic acid, N-(phosphonomethyl)glycine, 2-phosphonopropanoic acid, 3-phosphonopropanoic acid, 4-phosphonobutanoic acid, a phosphinosuccinic oligomer or a combination thereof.

The inversion surfactant having the structure of Formula 1 can be prepared by the following synthetic scheme:

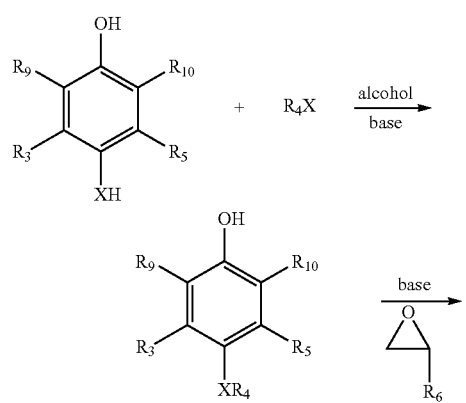

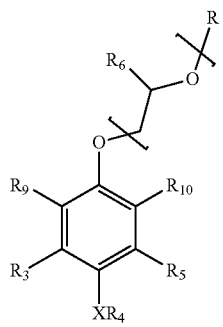

wherein X, $R_3$, $R_4$, $R_5$, $R_6$, $R_9$, $R_{10}$, and $R_{11}$ are defined as for Formula 1.

In the described polymer composition, the inversion surfactant having the structure of Formula 1 can have a concentration of from about 0.1 wt. % to about 10 wt. % based on the total weight of the polymer composition. Preferably, the inversion surfactant having the structure of Formula 1 has a concentration of from about 0.5 wt. % to about 5 wt. % based on the total weight of the polymer composition.

The water-in-oil polymer emulsion can further comprise an emulsifying agent. The surfactant or blend of surfactants can have a low hydrophile-lipophile balance (HLB) to aid preparation of an oil-continuous emulsion. Appropriate surfactants for water-in-oil emulsion polymerizations which are commercially available are compiled in the North American Edition of McCutcheon's Emulsifiers & Detergents. For example, the emulsifying agent can comprise nonionic ethoxylated fatty acid esters, ethoxylated sorbitan fatty acid esters, sorbitan esters of fatty acids such as sorbitan monolaurate, sorbitan monostearate, and sorbitan monooleate, block copolymers of ethylene oxide and hydroxyacids having a C10-C30 linear or branched hydrocarbon chain, linear or branched alcohol alkoxylates, or a combination thereof.

The emulsifying agent can be a single nonionic surfactant or blend thereof having a combined HLB value of about 2 to 10, for example about 3 to 10, or about 4 to 10, or about 5 to 10, or about 6 to 10, or about 7 to 10, or about 8 to 10, or about 2 to 9, or about 2 to 8, or about 2 to 7, or about 2 to 6, or about 2 to 5, or about 3 to 9, or about 4 to 8.

The water-in-oil emulsion can also comprise an alcohol alkoxylate. The alcohol alkoxylate can comprise a linear or branched alcohol ethoxylate, or a combination thereof.

The surfactant compositions, as described above, are useful as inverters (activators) of water-in-oil (inverse) emulsion polymers in various industries including for water clarification, papermaking, sewage and industrial water treatment, drilling mud stabilizers, and enhanced oil recovery.

The water-soluble or water-dispersible polymers useful in the polymer compositions include various polymers and their mixtures, or derivatives. The water-soluble or water-dispersible polymers used can be an anionic, a cationic, a nonionic, a zwitterionic, or an amphoteric polymer.

For example, the water-soluble or water-dispersible polymers contained in the polymer compositions can comprise polyacrylam ides, polyacrylates, copolymers thereof, and hydrophobically modified derivatives of these polymers.

Further, the water-soluble or water-dispersible polymers used in the polymer compositions described herein can include the water-soluble or water-dispersible polymers described in U.S. Pat. Nos. 3,624,019 and 3,734,873; the water-soluble or water-dispersible polymers can have various architectures as disclosed in EP 202780 (linear and cross-linked), and EP 374458, U.S. Pat. Nos. 5,945,494 and 5,961,840 (branched). Additionally, the water-soluble or water-dispersible polymers can contain hydrophobic monomers as disclosed in U.S. Pat. No. 4,918,123. These references are herein incorporated by reference for their various disclosures of water-soluble and water-dispersible polymers.

The polymers usefully incorporated in the polymer compositions typically have a weight average molecular weight (Mw) of about 500,000 Daltons to about 100,000,000 Daltons, or about 1,000,000 Daltons to about 50,000,000 Daltons, or about 5,000,000 Daltons to about 30,000,000 Daltons.

The water-soluble or water-dispersible polymer can comprise about 1 mol % to about 100 mol % acrylamide monomers, or about 1 mol % to about 90 mol %, or about 1 mol % to about 80 mol %, or about 1 mol % to about 70 mol %, or about 1 mol % to about 60 mol %, or about 1 mol % to about 50 mol %, or about 1 mol % to about 40 mol %, or about 1 mol % to about 30 mol %, or about 1 mol % to about 20 mol %, or about 1 mol % to about 10 mol %, or about 10 mol % to about 100 mol %, or about 20 mol % to about 100 mol %, or about 30 mol % to about 100 mol %, or about 40 mol % to about 100 mol %, or about 50 mol % to about 100 mol %, or about 60 mol % to about 100 mol %, or about 70 mol % to about 100 mol %, or about 80 mol % to about 100 mol %, or about 90 mol % to about 100 mol %, or about 20 mol % to about 80 mol, or about 30 mol % to about 70 mol %, or about 40 mol % to about 60 mol %, or about 60 mol % to about 80 mol % acrylamide monomers.

The water-soluble polymer or water-dispersible polymer can be present within the water-in-oil emulsion at about 15 wt % to 70 wt %, or about 17 wt % to 70 wt %, or about 19 wt % to 70 wt %, or about 21 wt % to 70 wt %, or about 23 wt % to 70 wt %, or about 25 wt % to 70 wt %, or about 15 wt % to 68 wt %, or about 15 wt % to 66 wt %, or about 15 wt % to 64 wt %, or about 15 wt % to 62 wt %, or about 15 wt % to 60 wt %, or about 15 wt % to 58 wt %, or about 15 wt % to 56 wt %, or about 25 wt % to 65 wt %, or about 30 wt % to 60 wt %, or about 30 wt % to 60 wt % based on the total weight of the emulsion.

Inverse emulsion polymers are prepared by dissolving the required monomers in the water phase, dissolving the emulsifying agent in the oil phase, emulsifying the water phase in the oil phase to prepare a water-in-oil emulsion, homogenizing the water-in-oil emulsion and polymerizing the monomers to obtain the polymer. A self-inverting surfactant may be added to the water-soluble polymer dispersed within the hydrocarbon matrix to obtain a self-inverting water-in-oil emulsion. Alternatively, a polymer solution can be made-up by inverting the polymer dispersed in oil in to water containing the surfactant.

Also present in the water-in-oil emulsion is an amount of water sufficient to form an aqueous (i.e. water) phase within the emulsion. Water is present in the water-in-oil emulsion at about 3 wt % to 50 wt %, or about 5 wt % to 50 wt %, or about 10 wt % to 50 wt %, or about 15 wt % to 50 wt %, or about 20 wt % to 50 wt %, or about 25 wt % to 50 wt %, or about 3 wt % to 35 wt %, or about 3 wt % to 30 wt %, or about 3 wt % to 25 wt %, or about 5 wt % to 45 wt %, or about 5 wt % to 40 wt %, or about 5 wt % to 35 wt %, based on the total weight of the water-in-oil emulsion.

The water-in-oil emulsion also contains an amount of oil sufficient to form an oil phase within the water-in-oil emulsion.

The oil in the oil phase can be a mixture of compounds, wherein the mixture is less than 0.1 wt % soluble in water at 25° C. and is a liquid over the range of 20° C. to 90° C.

The oil in the oil phase can comprise a linear, branched, or cyclic hydrocarbon moieties, aryl or alkaryl moieties, or combinations thereof.

The oil in the oil phase can have a density of about 0.8 g/L to 1.0 g/L, for example about 0.8 g/L to 0.9 g/L.

Examples of suitable oils for the oil phase can include a petroleum distillate, decane, dodecane, isotridecane, cyclohexane, toluene, xylene, and mixed paraffin solvents such as those sold under the trade name ISOPAR® by ExxonMobil Corp. of Irving, Tex.

The oil phase is present in the water-in-oil emulsion at about 10 wt % to 40 wt %, or about 15 wt % to 40 wt %, or about 20 wt % to 40 wt %, or about 22 wt % to 40 wt %, or about 24 wt % to 40 wt %, or about 26 wt % to 40 wt %, or about 28 wt % to 40 wt %, or about 30 wt % to 40 wt %, or about 10 wt % to 38 wt %, or about 10 wt % to 36 wt %, or about 10 wt % to 34 wt %, or about 10 wt % to 32 wt %, or about 10 wt % to 30 wt %, or about 10 wt % to 25 wt %, or about 10 wt % to 20 wt %, or about 15 wt % to 35 wt %, or about 20 wt % to 30 wt % based on the total weight of the water-in-oil emulsion.

The inversion surfactant of Formula I aids the inversion of the water-in-oil emulsion compared to a water-in-oil emulsion comprising no inversion surfactant or compared to a water-in-oil emulsion comprising a comparator inversion surfactant. The inversion surfactant of Formula I, of the present disclosure increase the speed and/or percent completion of the inversion process compared to a water-in-oil emulsion comprising no inversion surfactant or compared to a water-in-oil emulsion comprising a comparator inversion surfactant.

To aid inversion of a water-in-oil emulsion, the inversion surfactant is added to the emulsion at about 0.1 wt % to 20.0 wt % based on the total weight of the emulsion, or about 0.1 wt % to 15.0 wt %, or about 0.1 wt % to 10.0 wt %, or about 0.1 wt % to 7.5 wt %, or about 0.1 wt % to 5.0 wt %, or about 0.5 wt % to 4.5 wt %, or about 1.0 wt % to 4.0 wt %, or about 1.5 wt % to 3.5 wt %, or about 2.0 wt % to 3.0 wt %, or about 0.1 wt % to 4.5 wt %, or about 0.1 wt % to 4.0 wt %, or about 0.1 wt % to 3.5 wt %, or about 0.1 wt % to 3.0 wt %, or about 0.5 wt % to 5.0 wt %, or about 1.0 wt % to 5.0 wt %, or about 1.5 wt % to 5.0 wt %, or about 2.0 wt % to 5.0 wt %, based on the total weight of the emulsion.

The inversion surfactant can be added to the aqueous solution contacted with the emulsion to activate the polymer in a concentration of about 0.1 wt % to 20.0 wt % based on the total weight of the aqueous solution, or about 0.1 wt % to 15.0 wt %, or about 0.1 wt % to 10.0 wt %, or about 0.1 wt % to 7.5 wt %, or about 0.1 wt % to 5.0 wt %, or about 0.5 wt % to 4.5 wt %, or about 1.0 wt % to 4.0 wt %, or about 1.5 wt % to 3.5 wt %, or about 2.0 wt % to 3.0 wt %, or about 0.1 wt % to 4.5 wt %, or about 0.1 wt % to 4.0 wt %, or about 0.1 wt % to 3.5 wt %, or about 0.1 wt % to 3.0 wt %, or about 0.5 wt % to 5.0 wt %, or about 1.0 wt % to 5.0 wt %, or about 1.5 wt % to 5.0 wt %, or about 2.0 wt % to 5.0 wt %, based on the total weight of the aqueous solution.

The effective amount of the polymer composition can be from about 1 ppm to about 10000 ppm, from about 1 ppm to about 9000 ppm, from about 1 ppm to about 8000 ppm, from about 1 ppm to about 7000 ppm, from about 1 ppm to about 6000 ppm, from about 1 ppm to about 5000 ppm, from about 1 ppm to about 4000 ppm, from about 1 ppm to about 3000 ppm, from about 1 ppm to about 2000 ppm, from about 1 ppm to about 1000 ppm, based on the total weight of the process fluid. Preferably, the effective amount of the polymer composition is from about 1 ppm to about 900 ppm, from about 1 ppm, to about 800 ppm, from about 1 ppm to about 700 ppm, from about 1 ppm to about 600 ppm, or from about 1 ppm to about 500 ppm. Further, the effective amount of the polymer composition can be from about 1 ppm to about 250 ppm, from about 1 ppm to about 200 ppm, from about 1 ppm to about 100 ppm, from about 1 ppm to about 75 ppm, from about 1 ppm to about 50 ppm, from about 1 ppm to about 25 ppm, from about 1 ppm to about 15 ppm, or from about 1 ppm to about 10 ppm, based on the total weight of the process fluid.

The inversion and dilution to a target concentration of less than 1 wt % can be accomplished in about 1 to 15 minutes, for example about 1 to 14, 1 to 13, 1 to 12, 1 to 11, 1 to 10, 1 to 9, 1 to 8, 1 to 7, 1 to 6, 1 to 5, 2 to 15, 3 to 15, 4 to 15, 5 to 15, 6 to 15, 7 to 15, 8 to 15, 9 to 15, 10 to 15, 2 to 10, 2 to 9, 2 to 8, 2 to 7, 2 to 6, or 2 to 5 minutes.

After inversion, the aqueous solutions can comprise about 100 ppm to 10,000 ppm (0.01 wt % to 1.00 wt %) water-soluble or water-dispersible polymer, or about 200 ppm to 5000 ppm, or about 200 ppm to 4000 ppm, or about 200 ppm to 3000 ppm, or about 200 ppm to 2500 ppm water-soluble or water-dispersible polymer, based on the total weight of the aqueous solution.

As used herein, the term "polymer" means a water-soluble or water-dispersible polymer. The term "polymer" encompasses and includes homopolymers, copolymers, terpolymers and polymers with more than three monomers, cross-linked or partially crosslinked polymers, and combinations or blends of these.

As used herein, the term "polymer solution" or "polymer dispersion" means a polymer composition substantially dispersed or dissolved in water, a water source, or a water-based solution. Water-based solutions include one or more dissolved salts, buffers, acids, bases, surfactants, or other dissolved, dispersed, or emulsified compounds, materials, components, or combinations thereof.

As used herein, "inverse emulsion polymer" and "inverse latex polymer" mean a water-in-oil polymer emulsion comprising a water-soluble polymer (which could be cationic, anionic, nonionic, amphoteric polymer, or zwitterionic) according to this invention in the aqueous phase, a hydrocarbon oil for the oil phase and a water-in-oil emulsifying agent. Inverse emulsion polymers are hydrocarbon continuous with the water-soluble polymers dispersed within the hydrocarbon matrix. The inverse emulsion polymers are then "inverted" or activated for use by releasing the polymer from the particles using shear, dilution, and generally another surfactant. See U.S. Pat. No. 3,734,873, incorporated herein by reference.

As used herein, the term "water source" means a source of water comprising, consisting essentially of, or consisting of fresh water, deionized water, distilled water, produced water, municipal water, waste water such as runoff water or municipal waste water, treated or partially treated waste water, well water, brackish water, "gray water", sea water, or a combination of two or more such water sources as determined by context. A water source can include one or more salts, ions, buffers, acids, bases, surfactants, or other dissolved, dispersed, or emulsified compounds, materials, components, or combinations thereof.

As used herein, the terms "water-in-oil emulsion" mean a discontinuous internal water phase within a continuous oil phase, wherein the water phase includes at least one monomer or polymer. In general and as determined by context, these terms denote an emulsion prior to addition of inversion surfactants.

As used herein, the term "oil" or "hydrocarbon solvent" as applied to an oil phase of a water-in-oil emulsion, means any compound or blend thereof that is less than 0.1 wt % soluble in water at 25° C., is substantially chemically inert within a water-in-oil emulsion as described herein, and is a liquid over at least the range of 20° C. to 100° C.

As used herein, the term "water phase" means a water source having at least a monomer or polymer dispersed or dissolved therein, further wherein the dispersion or solution is a discontinuous phase within a water-in-oil emulsion.

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

The terms "aryl" or "ar" as used herein alone or as part of another group (e.g., arylalkyl) denote optionally substituted homocyclic aromatic groups, preferably monocyclic or bicyclic groups containing form 6 to 12 carbon atoms in the ring portion, such as phenyl, biphenyl, naphthyl, substituted phenyl, substituted biphenyl, or substituted naphthyl. Phenyl and substituted phenyl are the more preferred aryl groups. The term "aryl" also includes heteroaryl functional groups.

"Arylalkyl" means an aryl group attached to the parent molecule through an alkylene group. The number of carbon atoms in the aryl group and the alkylene group is selected such that there is a total of about 6 to about 18 carbon atoms in the arylalkyl group. A preferred arylalkyl group is benzyl.

The term "substituted," as in "substituted aryl," "substituted alkyl," and the like, means that in the group in question (i.e., the alkyl, aryl, or other group that follows the term), at least one hydrogen atom bound to a carbon atom is replaced with one or more substituent groups such as hydroxy (—OH), alkylthio, amido (—CON($R_A$)($R_B$), wherein $R_A$ and $R_B$ are wherein $R_A$ and $R_B$ are independently hydrogen, alkyl, or aryl), amino (—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

The term "heterocyclo," "heterocycle," or "heterocyclyl," as used herein, refers to a monocyclic, bicyclic, or tricyclic group containing 1 to 4 heteroatoms selected from N, O, S(O)$_n$, P(O)$_n$, PR$^z$, NH or NR$^z$, wherein R$^z$ is a suitable substituent. Heterocyclic groups optionally contain one or two double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2 yl, tetrahydrofuran-3-yl, imidazolidin-1-yl, imidazolidin-2 yl, imidazolidin-4-yl, pyrrolidin-1-yl, pyrrolidin-2 yl, pyrrolidin-3-yl, piperidin-1-yl, piperidin-2 yl, piperidin-3-yl, piperazin-1-yl, piperazin-2 yl, piperazin-3-yl, 1,3-oxazolidin-3-yl, isothiazolidine, 1,3-thiazolidin-3-yl, 1,2 pyrazolidin-2 yl, 1,3-pyrazolidin-1-yl, thiomorpholin-yl, 1,2 tetrahydrothiazin-2 yl, 1,3-tetrahydrothiazin-3-yl, tetrahydrothiadiazin-yl, morpholin-yl, 1,2 tetrahydrodiazin-2 yl, 1,3-tetrahydrodiazin-1-yl, 1,4-oxazin-2yl, and 1,2,5 oxathiazin-4-yl. Heterocyclic groups can be unsubstituted or substituted by one or more suitable substituents, preferably 1 to 3 suitable substituents, as defined above.

Having described the invention in detail, it will be apparent that modifications and variations are possible without departing from the scope of the invention defined in the appended claims.

EXAMPLES

The following non-limiting examples are provided to further illustrate the present invention.

Example 1: Synthesis of 4-(Octyloxyphenol)

The synthesis of 4-(octyloxy)phenol was completed using the reagents specified in Table 1 and according to the reaction depicted in Scheme 1, wherein R is octyl and X is bromo.

TABLE 1

Reagents for synthesis of 4-(octyloxyphenol)

| Reagent | Molecular Weight (g/mol) | Weight (g) | Weight (mol) | Mol reagent/ mol hydroquinone |
|---|---|---|---|---|
| Hydroquinone | 110.11 | 200 | 1.82 | 1.00 |
| 1-bromooctane | 193.12 | 293 | 1.52 | 0.84 |
| Potassium hydroxide | 56.10 | 100 | 2.00 | 0.98 |
| Potassium iodide | 166.02 | 0.2 | 0.001 | |
| Ethanol (reagent grade) | | 1200 | | |

Scheme 1. Synthesis of 4-(octyloxyphenol) (R = octyl, X = bromo)

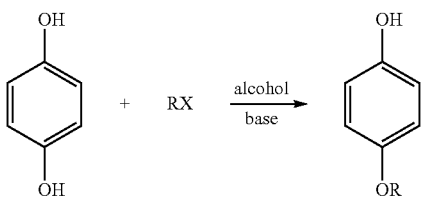

Dichloromethane, hexanes, distilled water, and concentrated hydrochloric acid were also used. Ethanol was charged to a 3-L four-necked reactor equipped with an overhead stirrer, nitrogen purge, temperature probe, a dropping funnel, and a condenser. The overhead stirrer was adjusted to a speed of approximately 500 rpm. A very slow nitrogen purge was started. Potassium hydroxide pellets were charged to the reactor. The reactor was heated to 40° C. and held for 30 minutes. Hydroquinone and potassium iodide were charged to the reactor and the reaction temperature was increased to 65° C.

Into a dropping funnel was charged 1-bromooctane, which was added into the reactor over a period of three hours, while maintaining stirring and temperature of 65° C. Stirring was continued at 65° C. until no 1-bromooctane was left in the solution as monitored by GC-MS. This process typically requires 8-10 hours.

The reaction was subsequently cooled to room temperature and acidified to a pH of 2.0 with concentrated hydrochloric acid. Approximately 300 mL deionized (DI) water was added and the reaction mixture was stirred for 15 minutes. The reaction mixture was extracted twice with 20 mL dichloromethane. The combined organic phase was then washed three times with 200 mL DI water, dried over $Na_2SO_4$, and concentrated in vacuo to provide off-white solids. The crude solids were washed with minimum amounts of cold hexanes to provide pure 4-(octyloxy)phenol. The sample was dried in a 40° C. oven.

Example 2: Addition of Ethylene Oxide to 4-(Octyloxy)Phenol

The following reagents and amounts thereof were used in the reaction: 570.00 g 4-(octyloxy)phenol of known concentration; 3.00 g potassium hydroxide (45% in water); about 30-35 mL heavy aromatic naphtha; ethylene oxide. The reaction proceeded according to Scheme 3, wherein R represents octyl, m represents an integer from 4 to 75, and n represents an integer from 0 to 20.

Scheme 3. Addition of ethylene oxide to 4-(octyloxy)phenol/ (R = octyl, n = 0 to 20, $R_{11}$ = H)

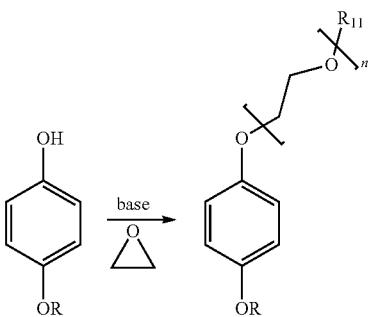

To a 1 L four-necked round bottom flask was added 4-(octyloxy)phenol and potassium hydroxide; the flask was equipped with an overhead stirrer, an nitrogen purge, a Dean-Stark trap with condenser, and a temperature probe. The stirrer was started at moderate speed, as the nitrogen purge was started at a rate of one bubble per second. The water flow was turned on to the condenser and the Dean-Stark trap was filled to the neck with heavy aromatic naphtha. The temperature was set to 150° C. and heating was started.

Water was distilled from the base catalyst. A 5 mL sample was collected for Karl-Fischer water analysis. If the sample contained more than 0.1 water, distillation was continued for 30 minutes and analysis was repeated.

When the sample contained less than 0.1% water, the flask was cooled to 60° C. Once the reaction mixture reached 60° C., the $N_2$ purge was increased. Under $N_2$ purge, the contents of the flask were poured into a tared nitrogen-filled one quart bottle. The contents of the bottle were then transferred to the Lab Oxyalkylation Unit Paar Reactor. The Paar Reactor was buttoned up and purged with nitrogen from three to four times. The pressure was set to 5 psi with nitrogen.

The reactor was heated to 150° C. Once stabilized, ethylene oxide was added until the pressure reached 60 psi. The weight of the ethylene oxide added to the reactor was recorded. The pressure was allowed to decrease, indicating a chemical reaction. When the pressure reached 10 psi, the desired amount of ethylene oxide needed to complete a one-mole addition was added, or until the pressure reached 60 psi. The pressure was continually allowed to decrease and ethylene oxide added until the pressure reached 60 psi until the desired amount of ethylene oxide was added and reacted.

Once the desired amount of ethylene oxide was added and reacted, a 50 mL sample was taken under safe conditions. This retrieved aliquot was recorded and the amount of ethylene oxide needed for the next one mole addition of EO was calculated. On the pressure reaching 10 psi, the desired amount of ethylene oxide needed to complete a one-mole addition was added, or until the pressure reached 60 psi. The pressure was allowed to decrease and the process was continued until the desired amount of ethylene oxide was added and consumed by the reaction. This same process was repeated until the entire ethylene oxide series was completed. The reaction mixture was removed from the Paar reactor. For each ethylene oxide sample, 5 g was submitted for NMR determination of actual ethylene oxide added.

Example 3: Inversion of Cationic and Non-Ionic Emulsion Polymers

The rate of inversion in the following examples was measured using a qualitative analytical tool referred to as a "torque monitor." It consisted of a DC stir motor, a controller that can report the torque (DC voltage) required to maintain a constant stir speed, and a computer to record the torque reading as a function of time.

All torque monitor tests were conducted at the 400 -g scale in a 600-mL beaker in tap water from the city of Naperville, Ill. at room temperature (approximately 22° C.) at the concentrations indicated unless otherwise noted. The solution was stirred at 300 rpm with a 1"×3" stainless-steel paddle positioned ½-inch from the bottom of the beaker and connected to the motor. Emulsion polymer was injected into the water vortex to start the experiment. Torque readings were collected every second and data worked-up in Microsoft Excel using a 20-period moving average.

The percent inversion at 2 minute and 5 minute was estimated from 2 and 5 minute torque readings compared to the final torque readings.

The activating surfactants used are listed in Table 2.

TABLE 2

| Activating surfactants used in Example 4 | |
|---|---|
| Name | Component |
| 4OP-10eo | 4-octyloxyphenol ethoxylate (9.9 ethylene oxide units) |
| Activator #1 | DOW TERGITOL NP-9.5 |
| Activator #2 | SASOL ALFONIC 1412-7 |
| Activator #3 | HUNTSMAN SURFONIC TDA-9 |

Example 3a: 1:1 Acrylamide/DMAEA.MCQ Emulsion Polymer

A 50 mole % cationic polymer without activating surfactant was synthesized as follows.

Monomer (aqueous) phase make-up: Into a 1-L beaker was added 227.7 g of a 49.5% aqueous acrylamide solution, 7.5 g adipic acid, 0.1 g sodium formate, and 52.5 g deionized water. The resulting components were stirred. To the resulting solution was added 0.13 g Versene 220 (tetrasodium ethylenediaminetetraacetate tetrahydrate available from Dow Chemical Company) and 384.1 g 80% DMAEA.MCQ (dimethylaminoethylacrylate methyl chloride quaternary salt) solution. The resulting mixture was stirred to produce a clear solution.

Oil phase preparation: Into a 2 L beaker was added 11.1 g sorbitan monooleate, 15.9 g SURFONIC L24-5 (a linear alcohol ethoxylate), and 270.0 g ISOPAR-M (a low odor, low aromatic hydrocarbon solvent of normal alkanes, isoalkanes, and cycloalkanes).

Emulsion make-up: The oil phase components were mixed with an IKA ULTRA TURAX T-25 (fine head) homogenizer at 11,000 rpm for about one minute resulting in a homogenous surfactant solution. While stirring at 11,000 rpm, the monomer phase was added to the beaker over a 30-second period. The resulting emulsion was homogenized for an additional 85 seconds. The final emulsion (297 cP, #2 spindle-30 rpm) was charged into a 2 L reactor and cooled to 6.9° C.

Polymerization: Polymerization was conducted under a nitrogen atmosphere. Initiation was accomplished by co-feeding 1.2 mL of a 1.2% sodium bromate solution at a rate between 0.79-2.78 mL/minute and 1 mL of a 0.58% sodium metabisulfite solution at a rate between 0.40-0.79 mL/minute in a manner that the temperature rise was about 1.5° C./min. At 34 min, the reaction temperature was 59.6° C., at which time the sodium bromate and sodium metabisulfite solution feed rates were held at 1.59 mL/minute and the reaction temperature controlled at 59.6° C. At one hour, the redox initiator feed stopped and 0.15 g of VAZO-64 was added to the reaction mixture to reduce the residual monomer. After an additional hour, the reaction mixture was cooled to room temperature yielding emulsion polymer 1 with a viscosity of 403 cP (#2 spindle/30 rpm), a median particle diameter size of 0.56 µm, and an RSV of 19.8 dL/g.

Polymer 1 blends with activating surfactants 1, 2, and 4OP-10eo were made in the following manner. Approximately 0.3 g of activating surfactant was added into a tared 1-oz. bottle containing a 1" magnetic stirring bar. Un-activated emulsion polymer 1 (i.e., emulsion polymer without an activating surfactant) was weighed into the bottle such that an activaated polymer with 1% activator was obtained. Exact weights are shown in Table 3. The resulting mixture was stirred for one hour and then allowed to equilibrate for at least two additional hours.

Polymer 1 blends with approximately 1.2% activator (Table 4) were obtained by adding the required amount of activator to polymer 1 blends containing approximately 1% activator. Polymer 1 blends with 1.4% activator were obtained similarly from the polymer 1 activator blends containing 1.2% activator (Table 5). With each successive addition of activating surfactant, the resulting mixture was stirred for one hour and allowed to equilibrate for at least an additional two hours.

TABLE 3

Polymer 1 blends with activating surfactants at approximately 1%

| Activator | Weight Activator (g) | Weight Emulsion 1 (g) | Wt. Percent Activator (%) |
|---|---|---|---|
| 4OP-10eo | 0.3110 | 29.7030 | 1.036 |
| Activator #1 | 0.3086 | 29.7034 | 1.028 |
| Activator #2 | 0.3077 | 29.7047 | 1.025 |

TABLE 4

Polymer 1 blends with activating surfactants at approximately 1.2%

| Activator | Wt. Remaining approximately 1% Polymer (g) | Weight. Activator (g) | Wt. Additional Activator (g) | Wt. Percent Activator (%) |
|---|---|---|---|---|
| 4OP-10eo | 25.7620 | 0.2669 | 0.0468 | 1.216 |
| Activator #1 | 25.5478 | 0.2627 | 0.0484 | 1.215 |
| Activator #2 | 25.5864 | 0.2623 | 0.0475 | 1.209 |

TABLE 5

Polymer 1 blends with activating surfactants at approximately 1.4%

| Activator | Wt. Remaining approximately 1.2% Polymer (g) | Weight. Activator (g) | Wt. Additional Activator (g) | Wt. Percent Activator (%) |
|---|---|---|---|---|
| 4OP-10eo | 21.4471 | 0.2607 | 0.0450 | 1.422 |
| Activator #1 | 20.9415 | 0.2545 | 0.0415 | 1.411 |
| Activator #2 | 20.4074 | 0.2467 | 0.0418 | 1.411 |

FIG. 1 depicts the inversion torque profile (0.5% invert) for polymer 1 with approximately 1% activating surfactant. The rate of inversion for polymer 1 with 4OP-10eo is faster than for polymer 1 with either activator 1 or 2.

Figure 2:
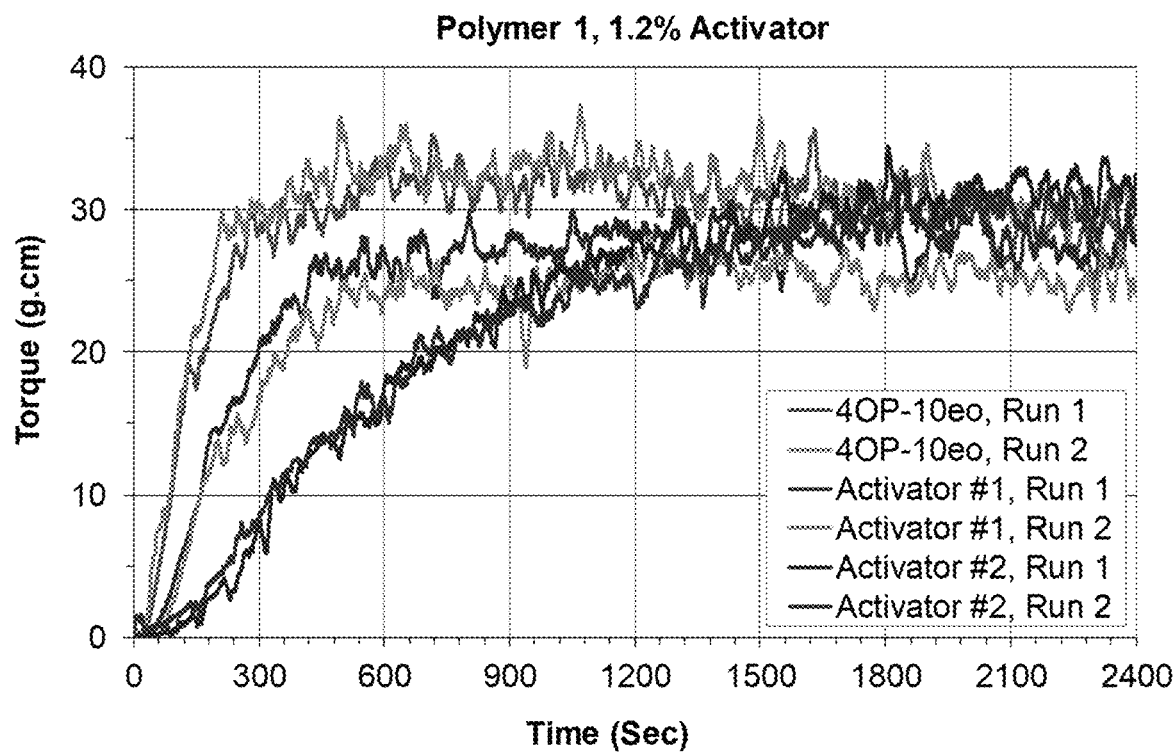
FIG. 2 is a graph of the torque versus time and shows the inversion torque profile (0.5% invert) for polymer 1 with approximately 1.2% activating surfactant.

FIG. 2 depicts the inversion torque profile (0.5% invert) for polymer 1 with approximately 1.2% activating surfactant. The rate of inversion for polymer 1 with 4OP-10eo is faster than for polymer 1 with either activator 1 or 2.

Figure 3:
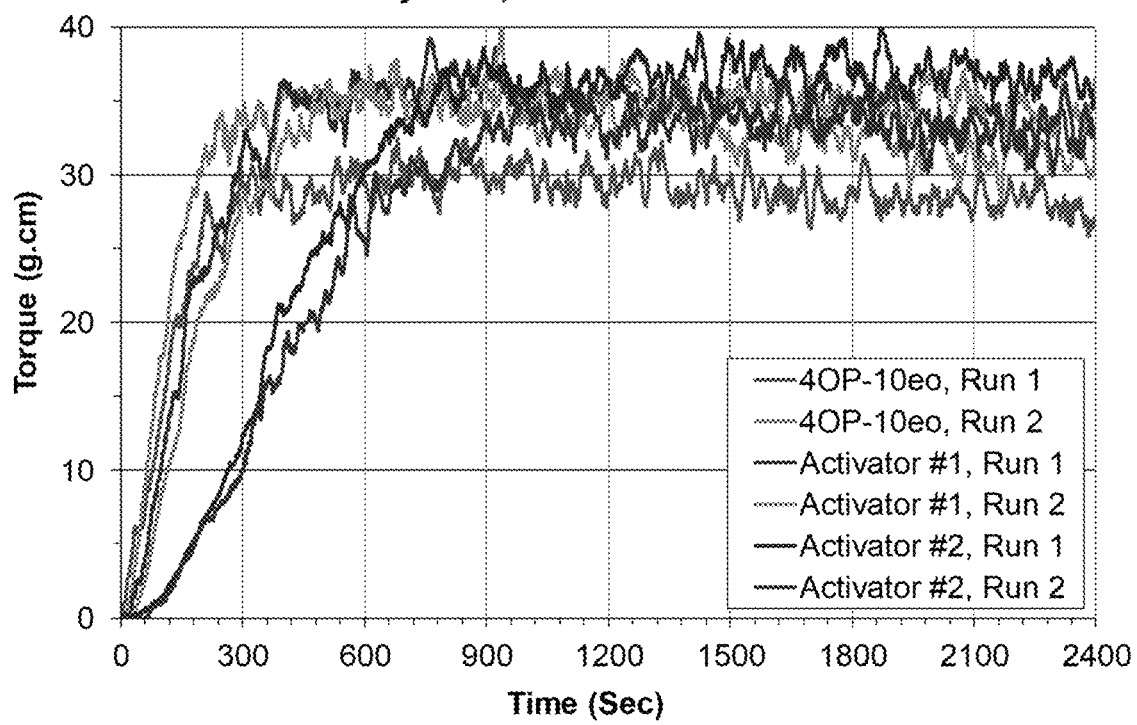
FIG. 3 is a graph of the torque versus time and shows the inversion torque profile (0.5% invert) for polymer 1 with approximately 1.4% activating surfactant.

FIG. 3 depicts the inversion torque profile (0.5% invert) for polymer 1 with approximately 1.4% activating surfactant. The rate of inversion for polymer 1 with 4OP-10eo and activator 1 are similar, but faster than for polymer 1 with activator 2.

Figure 4:
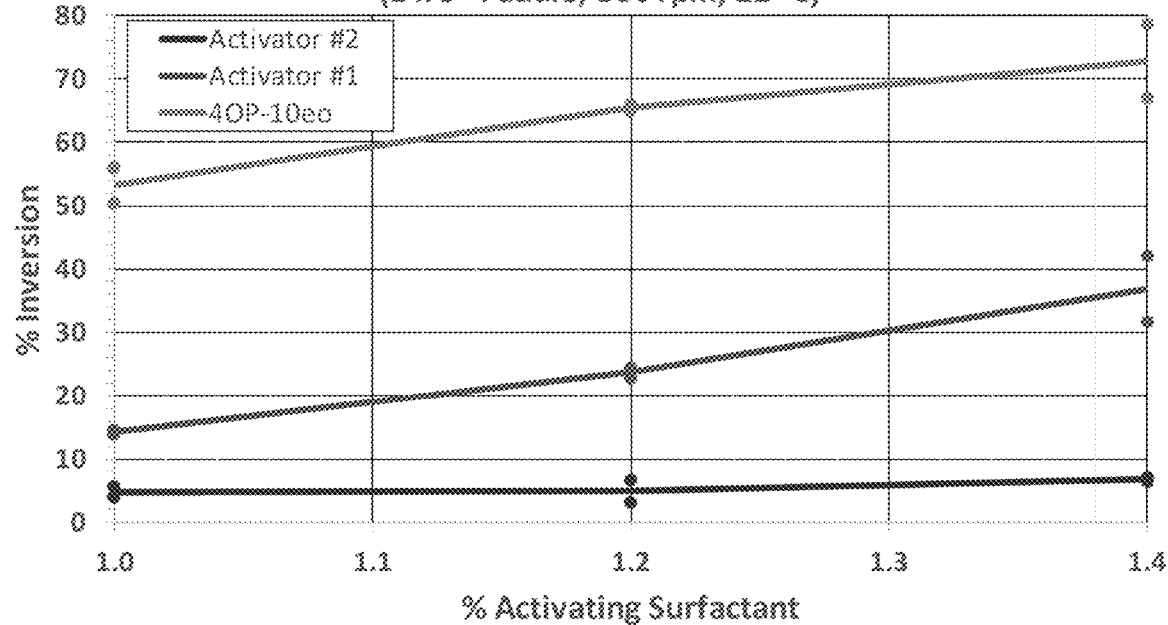
FIG. 4 is a graph of the percent inversion versus the percent activating surfactant and shows a comparison of the 2 minute percent inversion of polymer 1 with the activating surfactants.

FIG. 4 shows a comparison of the 2 minute percent inversion of polymer 1 with the activating surfactants. The percent inversion line is an average of two measurements (circles). The rate of inversion is faster for polymer 1 with 4OP-10eo than for polymer 1 with either activator 1 or 2 at equivalent activator concentrations.

Figure 5:
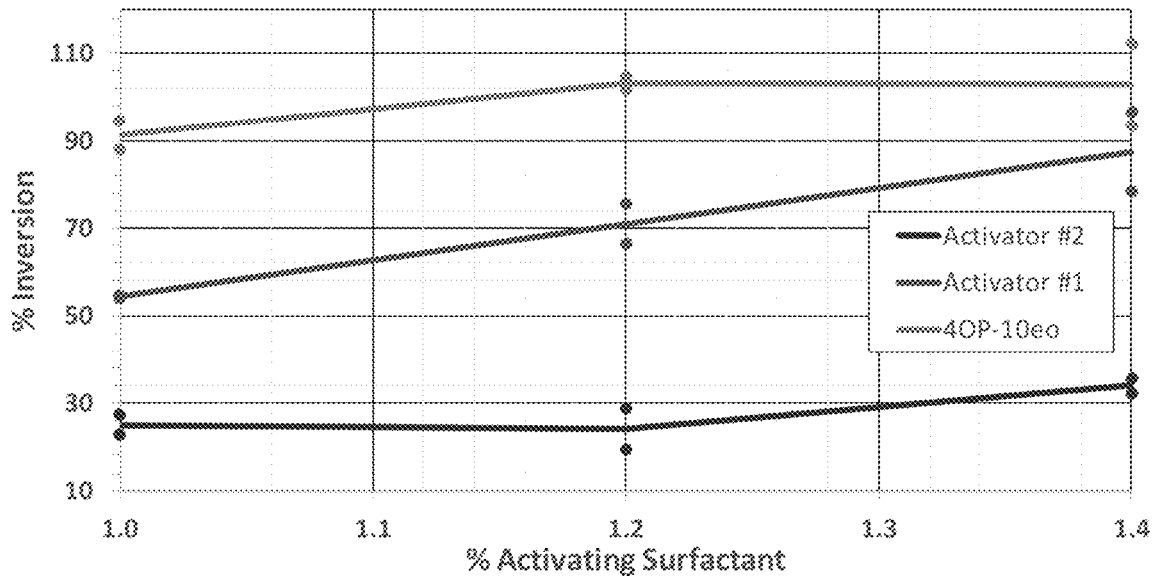
FIG. 5 is a graph of the percent inversion versus the percent activating surfactant and shows a comparison of the 5 minute percent inversion of polymer 1 with the activating surfactants.

FIG. 5 shows a comparison of the 5 minute percent inversion of polymer 1 with the activating surfactants. The percent inversion line is an average of two measurements (circles). The rate of inversion is faster for polymer 1 with 4O-10eo than for polymer 1 with either activator 1 or 2 at equivalent activator concentrations. Full inversion is observed for polymer 1 formulated with 1.2% 4OP-10eo at 5 minutes.

Example 3b: 7:3 Acrylamide/DADMAC Emulsion Polymer

An un-activated 7:3 acrylamide/DADMAC (polydiallyldimethylammonium chloride) emulsion co-polymer (emulsion polymer 2) without an activating surfactant was used in this example.

Emulsion polymer 2 was weighed into a 4 oz. bottle. Polymer 2 activator blends with approximately 2%, approximately 2.5%, and approximately 3% activator were made by blending activator into the emulsion while stirring. The resulting blends were stirred for one hour and allowed to stand for at least two hours before testing.

TABLE 6

Polymer 2 blends with activating surfactants at approximately 2%

| Activator | Weight Emulsion 1 (g) | Weight Activator (g) | Wt. Percent Activator (%) |
|---|---|---|---|
| 4OP-10eo | 70.36 | 1.47 | 2.05 |
| Activator #1 | 77.82 | 1.62 | 2.04 |
| Activator #3 | 70.04 | 1.45 | 2.03 |

TABLE 7

Polymer 2 blends with activating surfactants at approximately 2.5%

| Activator | Weight Emulsion 1 (g) | Weight Activator (g) | Wt. Percent Activator (%) |
|---|---|---|---|
| 4OP-10eo | 70.37 | 1.82 | 2.52 |
| Activator #1 | 71.78 | 1.82 | 2.47 |
| Activator #3 | 67.10 | 1.72 | 2.50 |

TABLE 8

Polymer 2 blends with activating surfactants at approximately 3%

| Activator | Weight Emulsion 1 (g) | Weight Activator (g) | Wt. Percent Activator (%) |
|---|---|---|---|
| 4OP-10eo | 97.02 | 3.03 | 3.03 |
| Activator #1 | 97.01 | 3.14 | 3.14 |
| Activator #3 | 97.01 | 3.02 | 3.02 |

Figure 6:
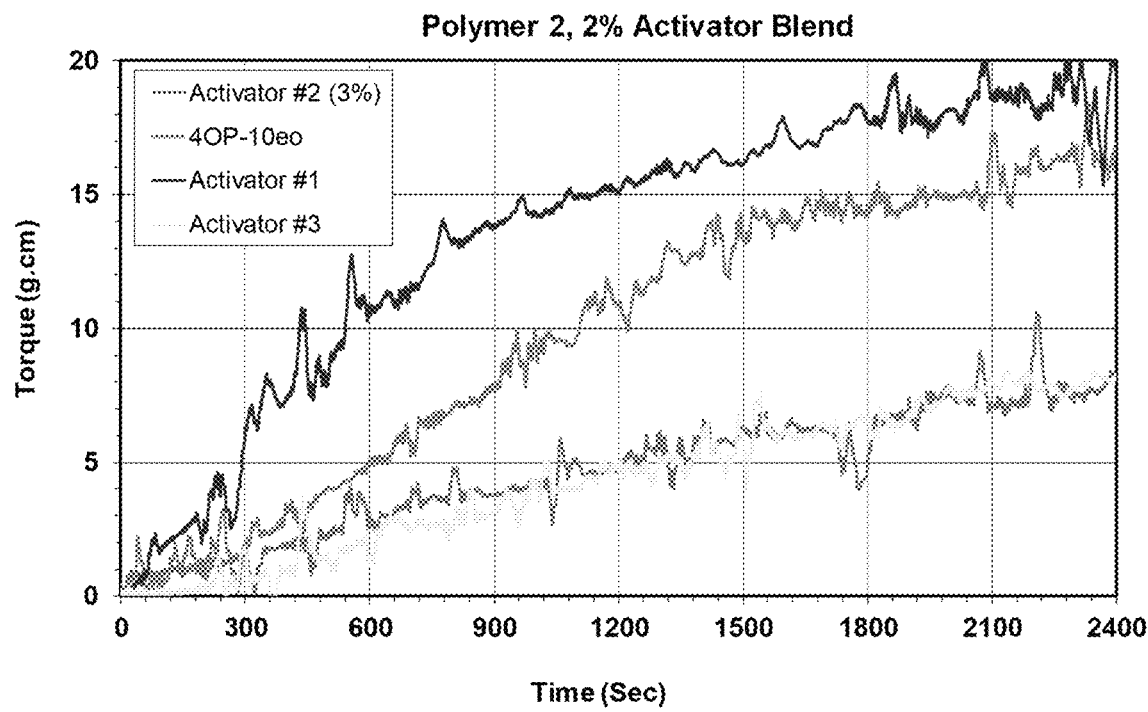
FIG. 6 is a graph of the torque versus time and shows the inversion torque profile (2% invert in DI water) for polymer 2 with approximately 2% activating surfactant.

FIG. 6 depicts the inversion torque profile (2% invert in DI water) for polymer 2 with approximately 2% activating surfactant. The rate of inversion for polymer 2 with activator 1 is faster than for polymer 2 with 4O-10eo. Both are faster than polymer 2 activated with activators 2 and 3.

Figure 7:
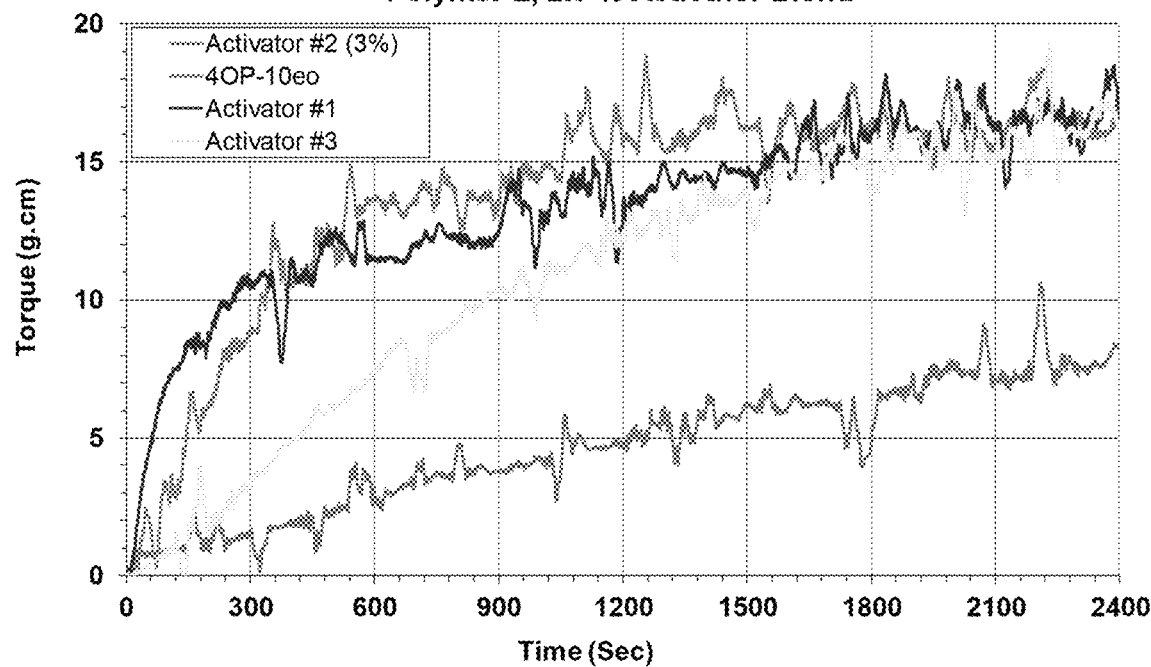
FIG. 7 is a graph of the torque versus time and shows the inversion torque profile (2% invert in DI water) for polymer 2 with approximately 2.5% activating surfactant.

FIG. 7 depicts the inversion torque profile (2% invert in DI water) for polymer 2 with approximately 2.5% activating surfactant. The inversion rates for polymer 2 activated with activator 1 and 4OP-10eo are similar. Both are faster than polymer 2 activated with activators 2 and 3.

Figure 8:
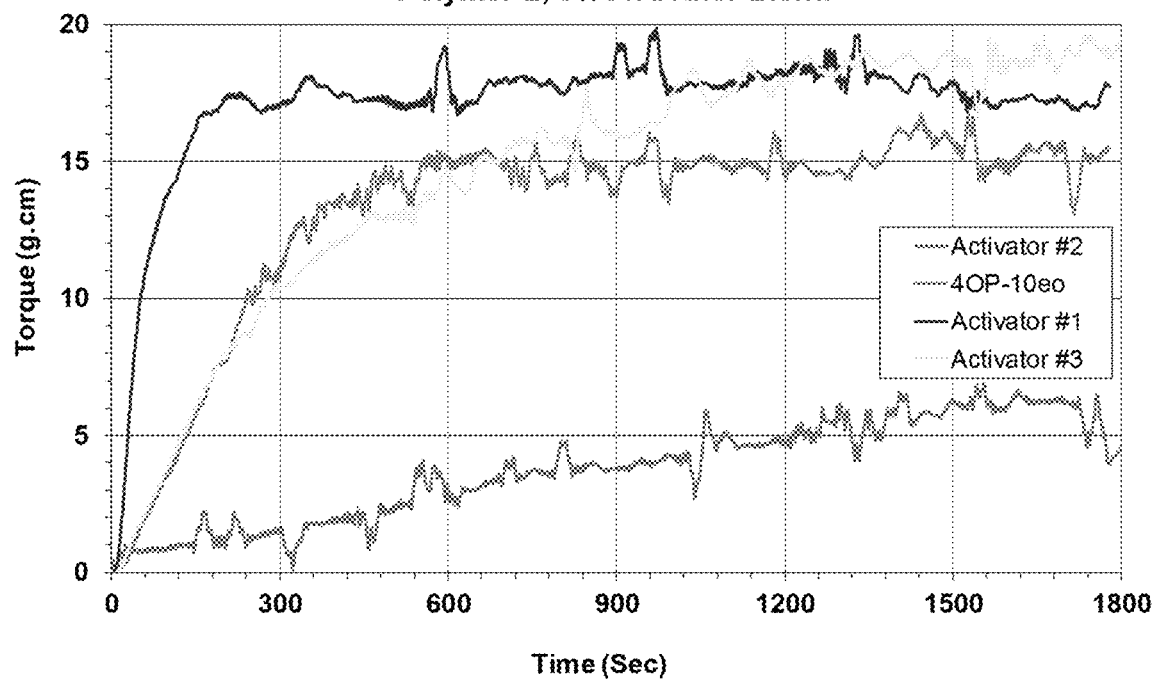
FIG. 8 is a graph of the torque versus time and shows the inversion torque profile (2% invert in DI water) for polymer 2 with approximately 3% activating surfactant.

FIG. 8 depicts the inversion torque profile (2% invert in DI water) for polymer 2 with approximately 3% activating surfactant. The inversion rate for polymer 2 with activator 1 has the fastest rate of inversion. The rates of inversion for polymer 2 with activators 3 and 4OP-10eo are similar. All activated polymers invert faster than polymer 2 with activator 2.

Figure 9:
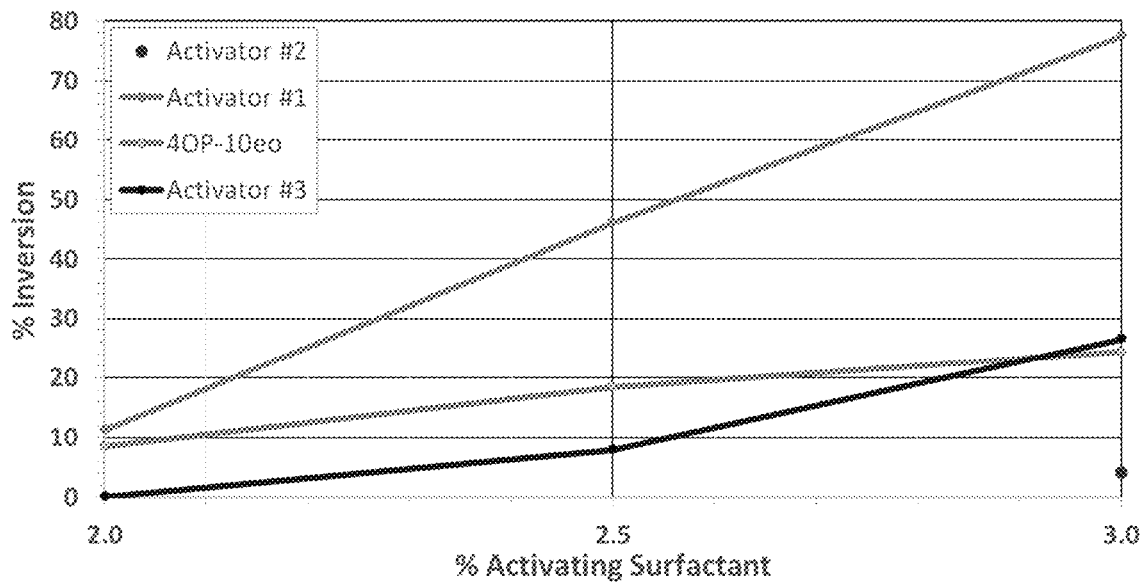
FIG. 9 is a graph of the percent inversion versus the percent activating surfactant and shows a comparison of the 2 minute percent inversion of polymer 2 with activating surfactants.

FIG. 9 shows a comparison of the 2 minute percent inversion of polymer 2 with activating surfactants. The 2 minute percent inversion for polymer 2 with activator 1 is greater than for the other polymers. The 2 minute percent inversion for polymer 2 with 4OP-10eo is greater than for polymer 2 with activator 3 at 2, 2.5% activator concentration, but similar with 3% activator.

Figure 10:
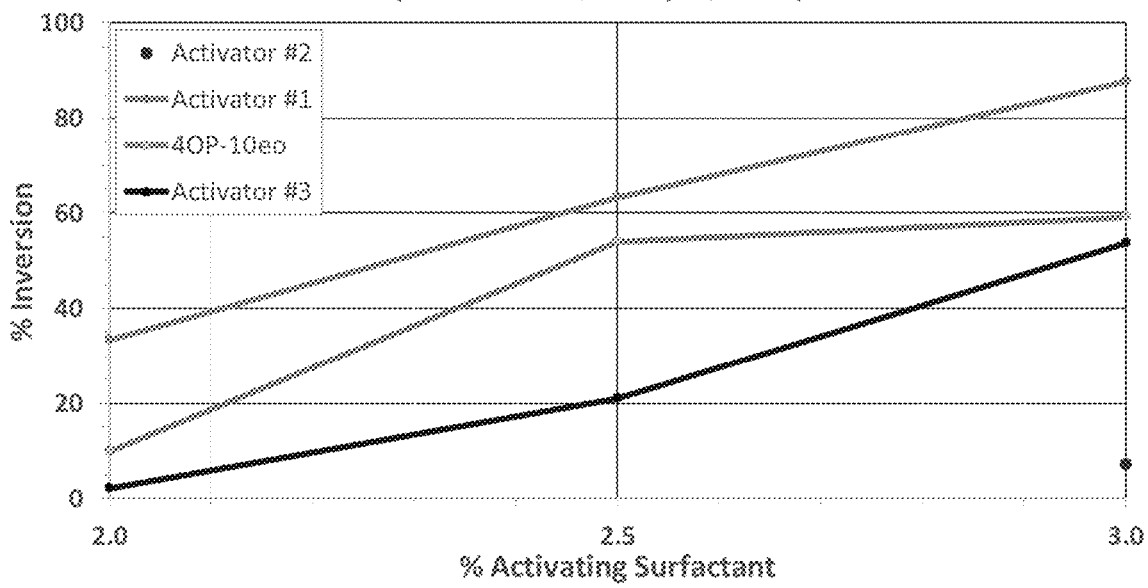
FIG. 10 is a graph of the percent inversion versus the percent activating surfactant and shows a comparison of the 5 minute percent inversion of polymer 2 with activating surfactants.

FIG. 10 shows a comparison of the 5 minute percent inversion of polymer 2 with activating surfactants. The 5 minute percent inversion for polymer 2 with activator 1 is greater than for the other polymers. The 5 minute percent inversion for polymer 2 with 4OP-10eo is greater than for polymer 2 with activator 3.

Example 3c: Poly(Acrylamide) Emulsion Polymer

Un-activated polyacrylamide emulsion polymer (emulsion polymer 3) without activating surfactant was used in this example.

Polymer 3 blends with approximately 1.8% activator (Table 10) were obtained by adding the required amount of activator to polymer 3 blends containing approximately 1.5% activator (Table 9). Polymer 3 blends with 2.1 and 2.4% activator were obtained similarly from the polymer 3 activator blends containing 1.8% activator (Tables 11 and 12). With each successive addition of activating surfactant, the resulting mixture was stirred for an hour and allowed to equilibrate for at least an additional two hours.

TABLE 9

Polymer 3 blends with activating surfactants at approximately 1.5%

| Activator | Weight Emulsion 1 (g) | Weight Activator (g) | Wt. Percent Activator (%) |
| --- | --- | --- | --- |
| 4OP-10eo | 100.75 | 1.53 | 1.50 |
| Activator #1 | 103.22 | 1.57 | 1.50 |
| Activator #2 | 109.69 | 1.67 | 1.50 |
| Activator #3 | 104.35 | 1.61 | 1.52 |

TABLE 10

Polymer 3 blends with activating surfactants at approximately 1.8%

| Activator | Wt. Remaining approximately 1% Polymer (g) | Weight. Activator (g) | Wt. Additional Activator (g) | Wt. Percent Activator (%) |
| --- | --- | --- | --- | --- |
| 4OP-10eo | 81.04 | 1.21 | 0.27 | 1.82 |
| Activator #1 | 84.10 | 1.26 | 0.28 | 1.83 |
| Activator #2 | 90.69 | 1.35 | 0.29 | 1.81 |
| Activator #3 | 83.27 | 1.26 | 0.26 | 1.83 |

TABLE 11

Polymer 3 blends with activating surfactants at approximately 2.1%

| Activator | Wt. Remaining approximately 1% Polymer (g) | Weight. Activator (g) | Wt. Additional Activator (g) | Wt. Percent Activator (%) |
| --- | --- | --- | --- | --- |
| 4OP-10eo | 62.28 | 1.13 | 0.19 | 2.12 |
| Activator #1 | 64.04 | 1.17 | 0.18 | 2.10 |
| Activator #2 | 72.65 | 1.32 | 0.21 | 2.10 |
| Activator #3 | 63.86 | 1.16 | 0.19 | 2.12 |

TABLE 12

Polymer 3 blends with activating surfactants at approximately 2.4%

| Activator | Wt. Remaining approximately 1% Polymer (g) | Weight. Activator (g) | Wt. Additional Activator (g) | Wt. Percent Activator (%) |
| --- | --- | --- | --- | --- |
| 4OP-10eo | 43.16 | 0.91 | 0.13 | 2.42 |
| Activator #1 | 43.89 | 0.92 | 0.12 | 2.37 |
| Activator #2 | 54.23 | 1.13 | 0.18 | 2.42 |
| Activator #3 | 45.31 | 0.96 | 0.13 | 2.40 |

Figure 11:
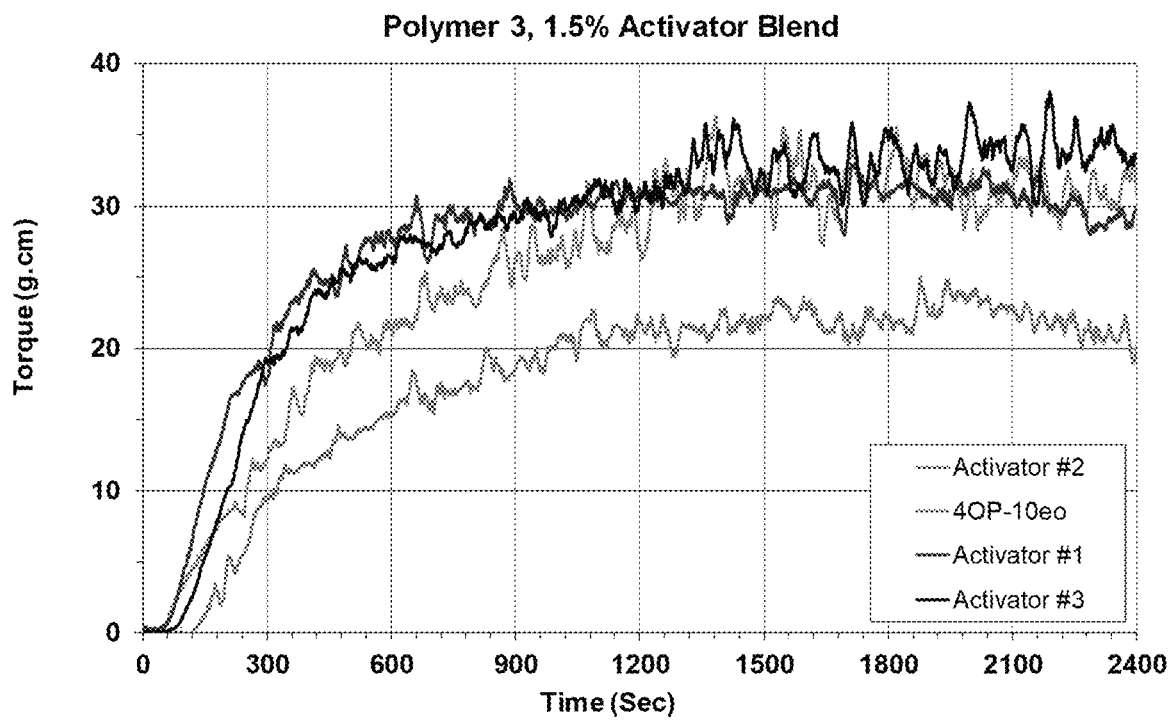
FIG. 11 is a graph of the percent inversion versus the percent activating surfactant and the inversion torque profile (2% invert) for polymer 3 with approximately 1.5% activating surfactant.

FIG. 11 depicts the inversion torque profile (2% invert) for polymer 3 with approximately 1.5% activating surfactant. Polymer 3 with activator 1 outperforms activator 3, which outperforms 4O-10eo, which outperforms activator 2.

Figure 12:
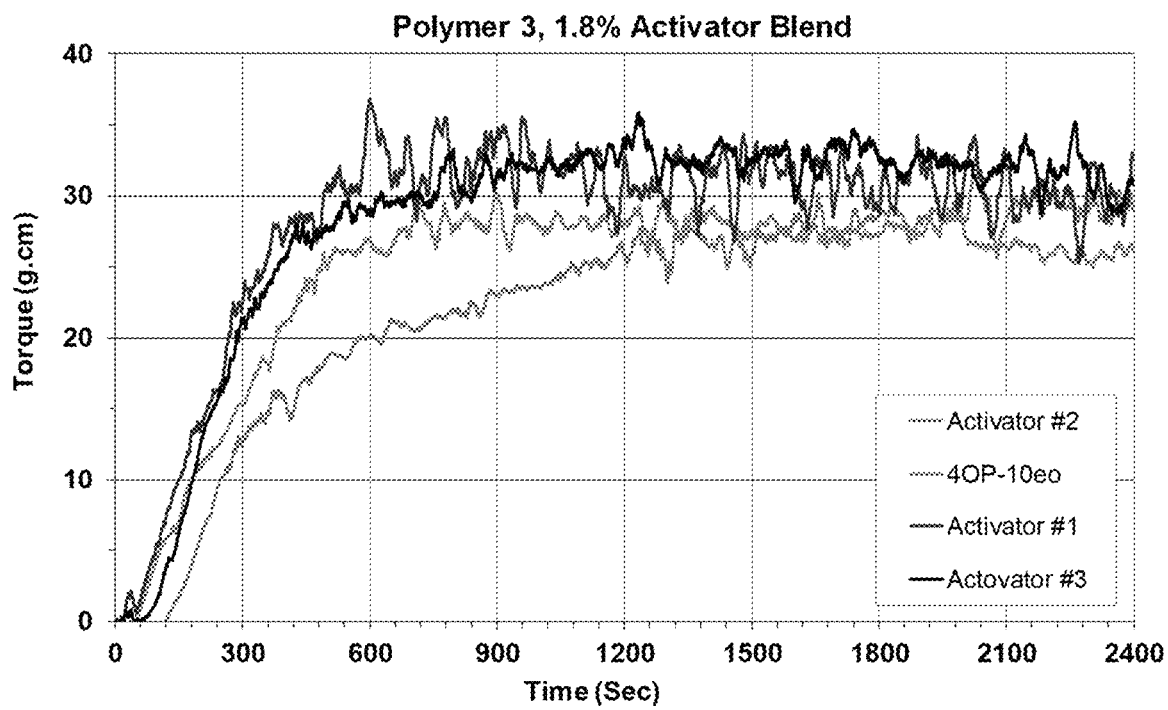
FIG. 12 is a graph of the percent inversion versus the percent activating surfactant and shows the inversion torque profile (2% invert) for polymer 3 with approximately 1.8% activating surfactant.

FIG. 12 depicts the inversion torque profile (2% invert) for polymer 3 with approximately 1.8% activating surfactant. Polymer 3 with activator 1 performs similarly to activator 3, which outperforms 4OP-10eo, which outperforms activator 2.

Figure 13:
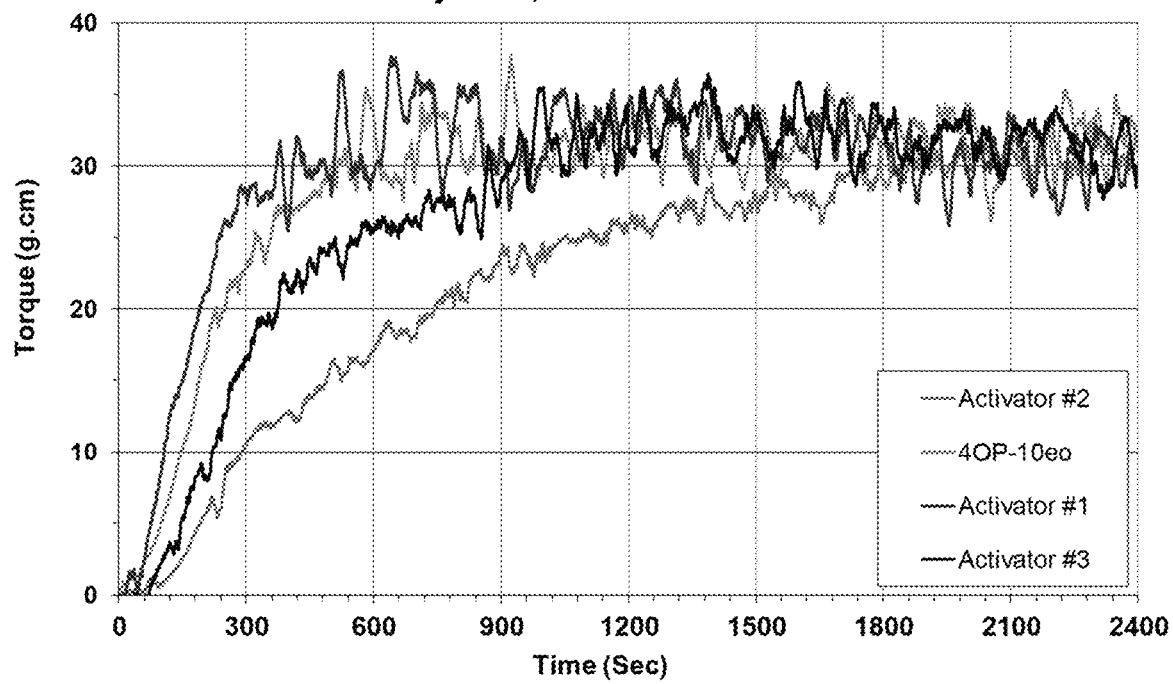
FIG. 13 is a graph of the percent inversion versus the percent activating surfactant and shows the inversion torque profile (2% invert) for polymer 3 with approximately 2.1% activating surfactant.

FIG. 13 depicts the inversion torque profile (2% invert) for polymer 3 with approximately 2.1% activating surfactant. Polymer 3 with activator 1 outperforms 4OP-10eo, which outperforms activator 3, which outperforms activator 2.

Figure 14:
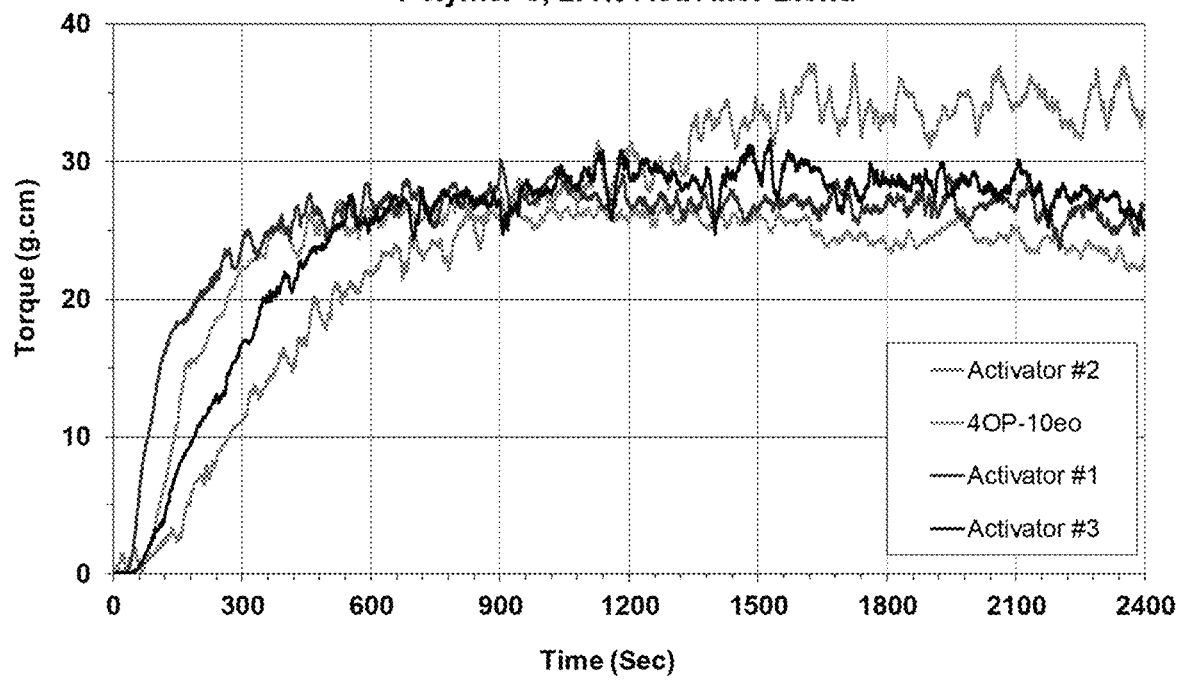
FIG. 14 is a graph of the percent inversion versus the percent activating surfactant and the inversion torque profile (2% invert) for polymer 3 with approximately 2.4% activating surfactant.

FIG. 14 depicts the inversion torque profile (2% invert) for polymer 3 with approximately 2.4% activating surfactant. Polymer 3 with activator 1 outperforms 4OP-10eo, which outperforms activator 3, which outperforms activator 2.

Figure 15:
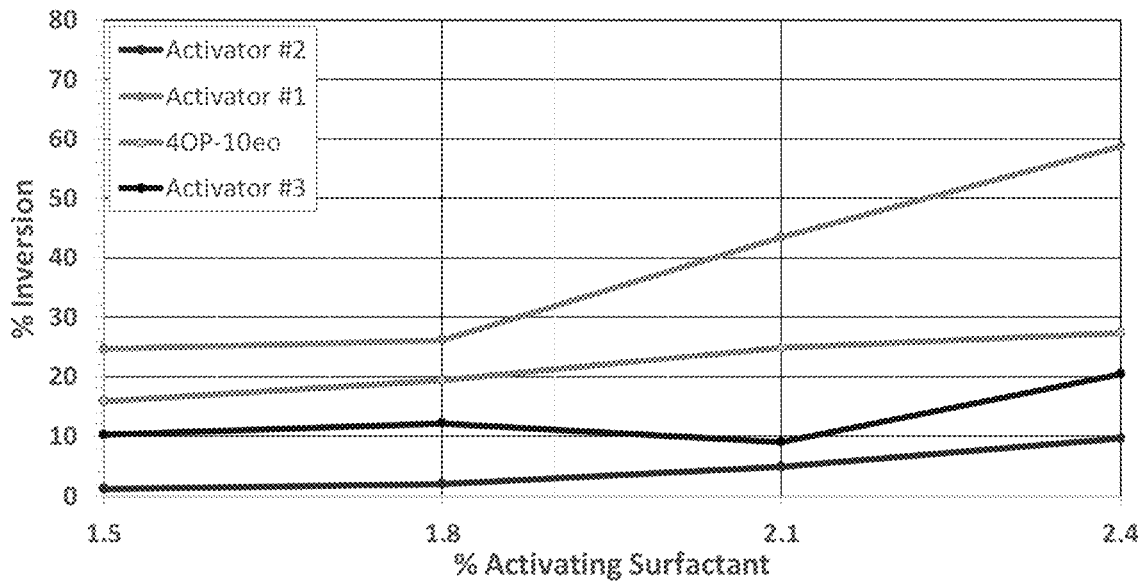
FIG. 15 is a graph of the percent inversion versus the percent activating surfactant and shows a comparison of the 2 minute percent inversion of polymer 3 with activating surfactants.

FIG. 15 shows a comparison of the 2 minute percent inversion of polymer 3 with activating surfactants. The 2 minute percent inversion for polymer 3 with activator 1 is greater than for the other polymers. The 2 minute percent inversion for polymer 3 with 4OP-10eo is greater than for polymer 2 with activators 2 and 3.

Figure 16:
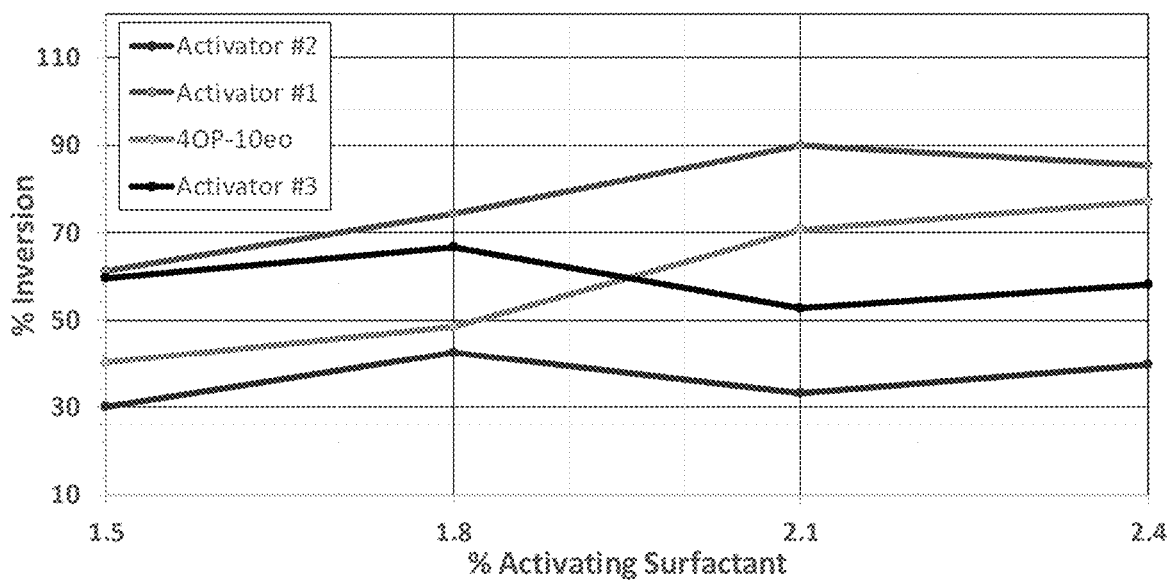
FIG. 16 is a graph of the percent inversion versus the percent activating surfactant and shows a comparison of the 5 minute percent inversion of polymer 3 with activating surfactants.

FIG. 16 shows a comparison of the 5 minute percent inversion of polymer 3 with activating surfactants. The 5 minute percent inversion for polymer 3 with activator 1 is greater than for the other polymers. The 5 minute percent inversion for polymer 3 with 4OP-10eo is less than for polymer 3 with activator 3 at 1.5 and 1.8% activating surfactant. The relative 5 minute percent inversion crosses, and at 2.1 and 2.4% activator polymer 3 with 4OP-10eo is greater than for polymer 3 with activator 3.

The inversion conditions employed in Examples 3a-3c (1"×3" paddle, 300 rpm) simulated inversion under "low shear" conditions. There is a benefit of having polymers that make-down efficiently under these conditions as this allows reduction of capital expenditures by use of less complex make-down equipment and elimination of inverted polymer aging tanks.

Polymer 1 was synthesized using a combination of sorbitan monooleate and a linear alcohol ethoxylate (7 eo) required 1.4% Activator #3 to meet an inversion of greater than 90%. Unexpectedly for Polymer 1, the Polymer 1 blend with 4OP-10eo inverted better than the blends with the DOW TERGITOL NP-9.5 or the standard linear alcohol ethoxylate (Activator #2). At 5 minutes, full inversion was observed for Polymer 1 with 1.2% 4OP-10eo (FIG. 5).

Polymer 2 was formulated with 2.7% Activator #2 to meet an inversion of greater than 90%. With 2.5% activating surfactant, the rate of inversion of Polymer 2 with 4OP-10eo approached that of Polymer 2 with TERGITOL NP-9.5 (FIG. 7). Both of these activated polymers inverted better than Polymer 2 with the linear alcohol ethoxylates (Activators 2 and 3).

Polymer 3 was formulated with 2.35% Activator #2 to meet an inversion of greater than 90%. As observed for Polymer 2, with 2.4% activating surfactant, the rate of inversion of Polymer 3 with 4OP-10eo approached that of Polymer 3 with Tergitol NP-9.5 (FIG. 14). Both of these activated polymers inverted better than Polymer 3 with the linear alcohol ethoxylates (Activators 2 and 3).

Example 4: Inversion of Anionic Emulsion Polymers

The performance of certain surfactants for inversion of anionic emulsion polymers was determined by torque monitor technique as described in Example 3, with some modifications described below.

Torque monitor tests were conducted at the 500 g scale in a 1000-mL beaker in different waters (tap water from the City of Naperville, Ill.; synthetic sea water; high TDS brine) at room temperature (approximately 22° C.) at the concentrations indicated in the examples unless otherwise noted. The solution was stirred at 400 rpm with a 1 an HS-1 2.65 inch cage stirrer positioned ½ inch from the bottom of the beaker and connected to the motor. Emulsion polymer was injected into the water vortex to start the experiment. Torque readings were collected every second and data worked-up in Microsoft Excel using a 20-period moving average.

The percent inversion at 2 minute and 5 minute was estimated from 2 and 5 minute torque readings compared to the final torque readings.

The activating surfactants used are listed in Table 13.

TABLE 13

Activating surfactants used in Example 4

| Name | Component |
| --- | --- |
| 4OP-nEO | 4-octyloxyphenol ethoxylate (where n indicates moles of EO units) |
| Activator #1 | DOW TERGITOL NP-9.5 |
| Activator #2 | SASOL ALFONIC 1412 7 |
| Activator #3 | HUNTSMAN SURFONIC TDA-9 |

Example 4a: 7:3 Acrylamide/Acrylic Acid Emulsion Polymer—Inversion in Tap Water

Un-activated 7:3 acrylamide/acrylic acid emulsion co-polymer (emulsion polymer 4) without activating surfactant was used in this example.

Emulsion polymer 4 was weighed into a 4 oz. bottle. Polymer 4 activator blends with approximately 1.35% activator were made by blending activator into the emulsion while stirring. The resulting blends were stirred for one hour and allowed to stand for at least two hours before testing.

TABLE 14

Polymer 4 blends with activating surfactants at approximately 1.35%

| Activator | Weight Emulsion 4 (g) | Weight Activator(g) | Wt. Percent Activator (%) |
| --- | --- | --- | --- |
| Activator #1 | 74.012 | 1.013 | 1.35% |
| Activator #2 | 74.098 | 1.018 | 1.36% |
| Activator #3 | 74.008 | 1.020 | 1.35% |
| 4OP-10EO | 74.912 | 1.016 | 1.34% |
| 4OP-8.5EO | 74.013 | 1.013 | 1.35% |
| 4OP-7.2EO | 74.121 | 1.012 | 1.35% |

Figure 17:
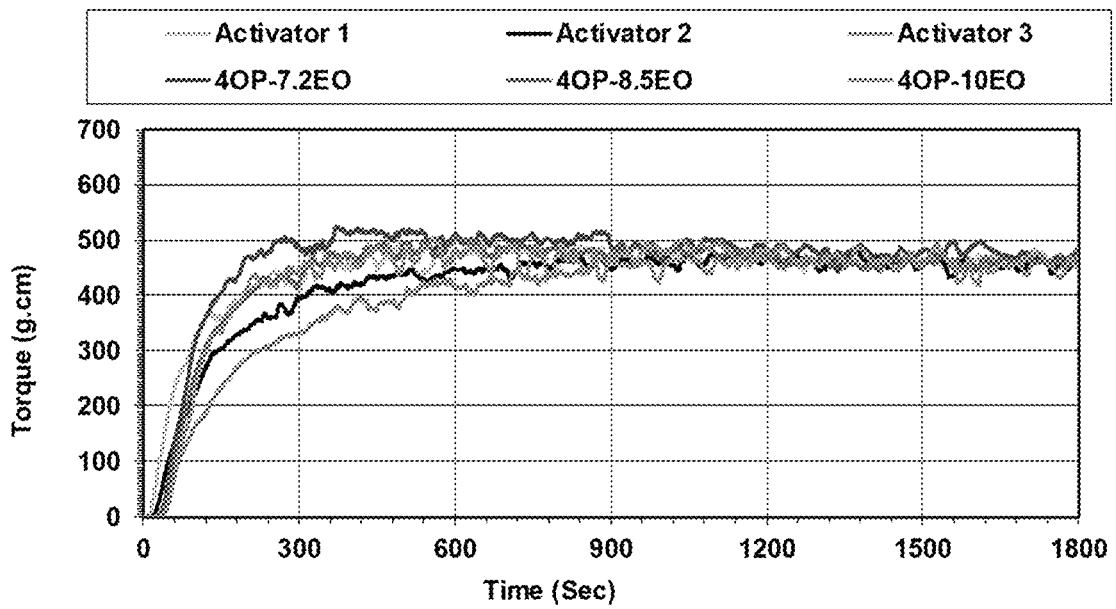
FIG. 17 is a graph of the torque versus time and shows the inversion torque profile (0.5% invert in tap water) for polymer 4 with approximately 1.35% activating surfactant.

FIG. 17 depicts the inversion torque profile (0.5% invert in tap water) for polymer 4 with approximately 1.35% activating surfactant. The inversion rates for polymer 4 activated with activator 1 and 4OP-7.2EO are similar. Polymer 4 blends with all 4OP-nEO activators are faster than polymer 4 activated with activators 2 and 3.

Figure 18:
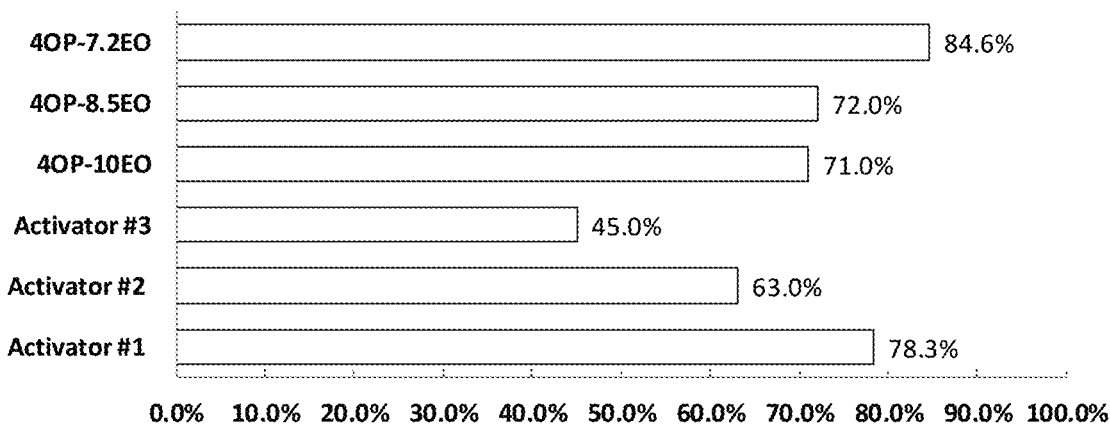
FIG. 18 shows a comparison of the 2 minute percent inversion of polymer 4 with activating surfactants.

FIG. 18 shows a comparison of the 2 minute percent inversion of polymer 4 with activating surfactants. The 2 minute percent inversion for polymer 4 with 4OP-7.2EO was greater than for the other polymers.

Figure 19:
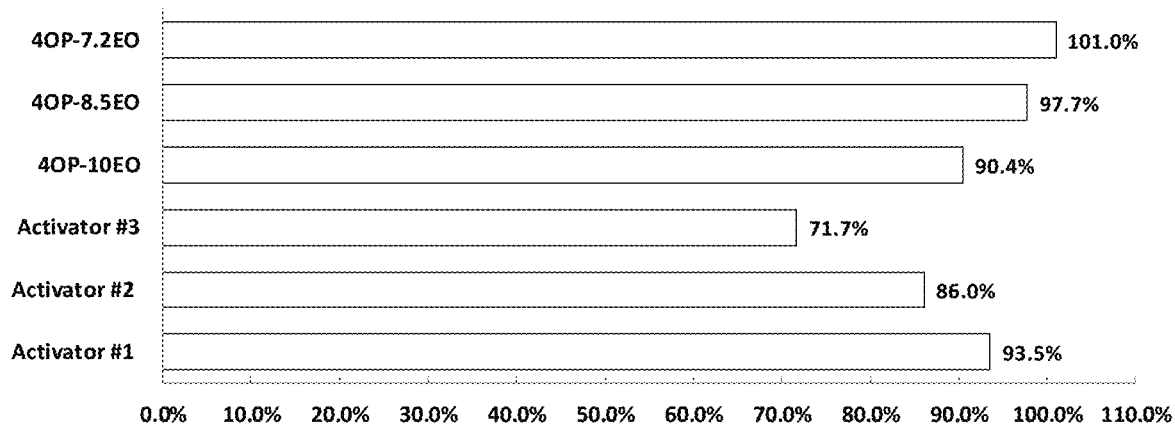
FIG. 19 shows a comparison of the 5 minute percent inversion of polymer 4 with activating surfactants.

FIG. 19 shows a comparison of the 5 minute percent inversion of polymer 4 with activating surfactants. The 5 minute percent inversion for polymer 4 with 4OP-7.2EO was greater than for the other polymers.

Example 4b: 7:3 Acrylamide/Acrylic Acid Emulsion Polymer—Inversion in Synthetic Sea Water Un-activated 7:3 acrylamide/acrylic acid emulsion co-polymer (emulsion polymer 5) without activating surfactant was used in this example.

Emulsion polymer 5 was weighed into a 4. oz bottle. Polymer 4 activator blends with approximately 2.5% activator were made by blending activator into the emulsion while stirring. The resulting blends were stirred for one hour and allowed to stand for at least two hours before testing.

TABLE 15

Polymer 5 blends with activating surfactants at approximately 1.35%

| Activator | Weight Emulsion 5 (g) | Weight Activator(g) | Wt. Percent Activator (%) |
| --- | --- | --- | --- |
| Activator #1 | 97.512 | 2.509 | 2.51% |
| Activator #2 | 97.489 | 2.491 | 2.49% |
| Activator #3 | 97.521 | 2.502 | 2.50% |
| 4OP-8EO | 97.591 | 2.507 | 2.50% |
| 4OP-9EO | 97.492 | 2.509 | 2.51% |
| 4OP-10EO | 97.511 | 2.501 | 2.50% |

Preparation of Synthetic Sea Water (SSW):
The 3.5% synthetic seawater used in the present Example was prepared by blending the components of Table 16. SSW was filtered through a WHATMAN 1 filter by suction filtration to remove any particulate.

TABLE 16

Ingredients of 3.5% SSW

| Reagent | Amount (g) |
| --- | --- |
| Sodium chloride (NaCl) | 24.65 |
| Calcium chloride CaCl2•2H2O | 1.57 |
| Magnesium chloride (MgCl2•6H2O) | 11.39 |
| Sodium bicarbonate (NaHCO$_3$) | 0.01 |
| Sodium sulfate (Na2SO4) | 4.38 |
| Deionized water | 957.99 |

Figure 20:
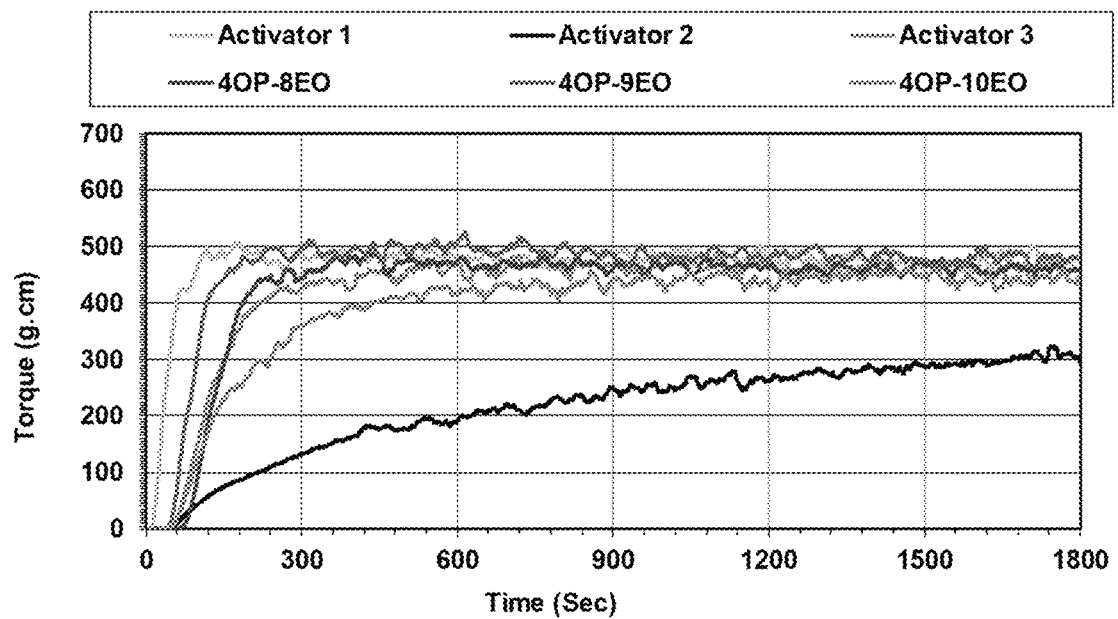
FIG. 20 is a graph of the torque versus time and shows the inversion torque profile (1% invert in SSW) for polymer 4 with approximately 2.5% activating surfactant.

FIG. 20 depicts the inversion torque profile (1% invert in SSW) for polymer 4 with approximately 2.5% activating surfactant. The rate of inversion for polymer 5 with activator 1 was faster than for other polymers. The rate of inversion for polymer 4 with activator 4OP-9EO was faster than polymer 5 with activator 2 and activator 3.

Figure 21:
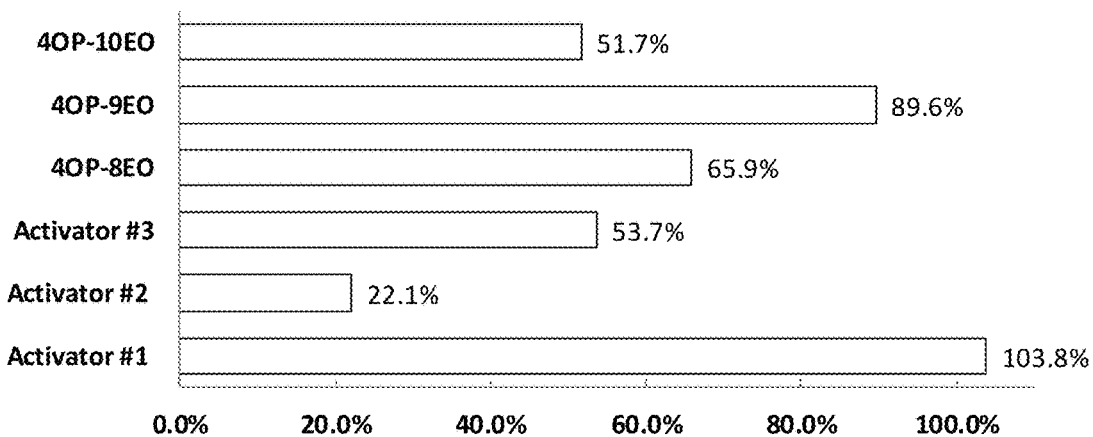
FIG. 21 shows a comparison of the 2 minute percent inversion of polymer 5 with activating surfactants.

FIG. 21 shows a comparison of the 2 minute percent inversion of polymer 5 with activating surfactants. The 2 minute percent inversion for polymer 5 with activator 1 was greater than for the other polymers.

Figure 22:
FIG. 22 shows a comparison of the 5 minute percent inversion of polymer 5 with activating surfactants.

FIG. 22 shows a comparison of the 5 minute percent inversion of polymer 5 with activating surfactants. The 5 minute percent inversion for polymer 5 with activator 1 was greater than for the other polymers.

Example 4c: 7.5:2.5 Acrylamide/ATBS Emulsion Polymer—Inversion in SSW

A 7.5:2.5 acrylamide/ATBS (acrylamido tertiary butyl sulfonic acid) emulsion co-polymer (emulsion polymer 6) without activating surfactant was used in this example.

Emulsion polymer 6 was weighed into a 4 oz. bottle. Polymer 4 activator blends with approximately 2.5% activator were made by blending activator into the emulsion while stirring. The resulting blends were stirred for one hour and allowed to stand for at least two hours before testing.

TABLE 17

Polymer 6 blends with activating surfactants at approximately 2%

| Activator | Weight Emulsion 4 (g) | Weight Activator(g) | Wt. Percent Activator (%) |
|---|---|---|---|
| Activator #1 | 98.011 | 2.013 | 2.01% |
| Activator #2 | 98.107 | 2.028 | 2.03% |
| Activator #3 | 98.197 | 2.012 | 2.01% |
| 4OP-8EO | 98.056 | 2.022 | 2.02% |
| 4OP-9EO | 98.151 | 2.028 | 2.02% |
| 4OP-10EO | 98.101 | 1.9977 | 2.00% |

Figure 23:
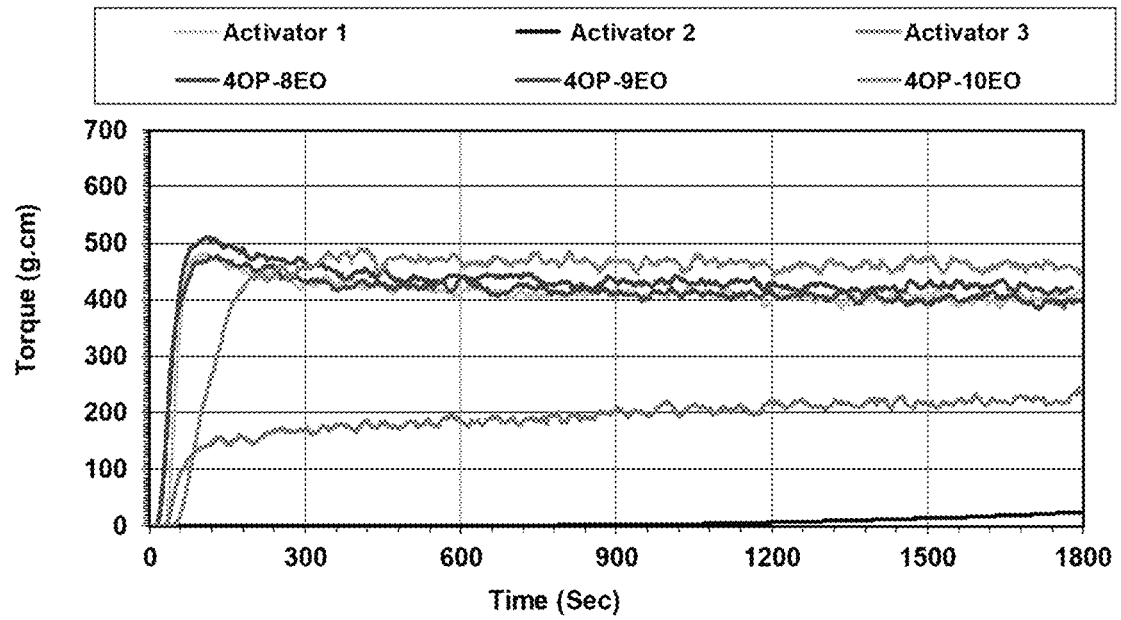
FIG. 23 is a graph of the torque versus time and shows the inversion torque profile (1% invert in SSW) for polymer 6 with approximately 2.0% activating surfactant.

FIG. 23 depicts the inversion torque profile (1% invert in SSW) for polymer 6 with approximately 2.0% activating surfactant. The rate of inversion for polymer 6 with activator 1, 4OP-8EO and 4OP-9EO are similar. Polymer 6 blends with all 4OP-nEO activators are faster than polymer 4 with activators 2 and 3. Polymer 5 blend with activator 2 failed the torque test.

Figure 24:
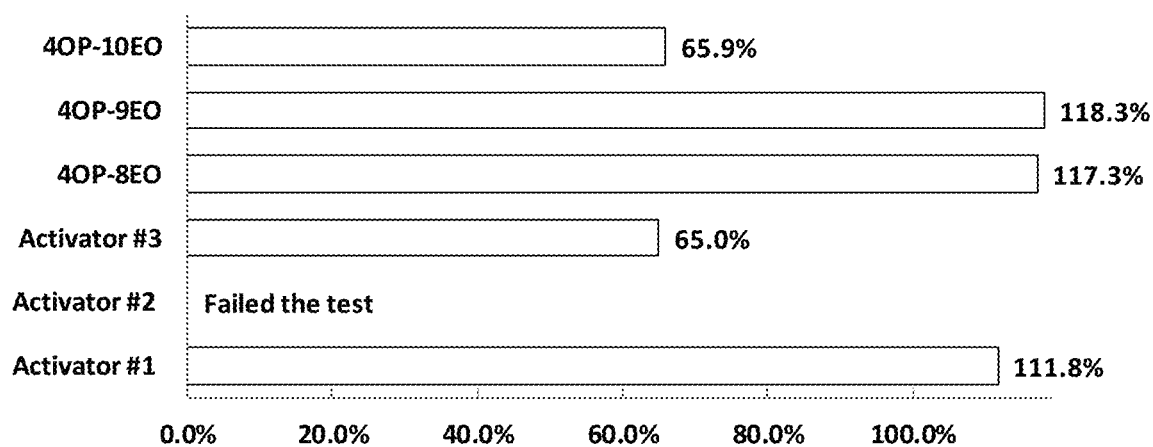
FIG. 24 shows a comparison of the 2 minute percent inversion of polymer 6 with activating surfactants.

FIG. 24 shows a comparison of the 2 minute percent inversion of polymer 6 with activating surfactants. The polymer 6 blends with 4OP-8EO, 4OP-9EO, and activator 1 invert fully in 2 minutes.

Figure 25:
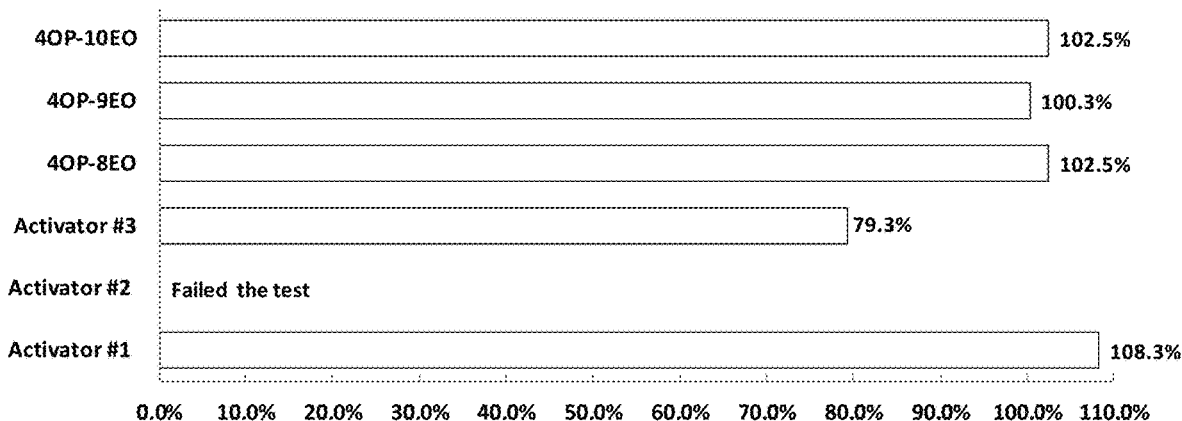
FIG. 25 shows a comparison of the 5 minute percent inversion of polymer 6 with activating surfactants.

FIG. 25 shows a comparison of the 5 minute percent inversion of polymer 6 with activating surfactants. The polymer 6 blends with 4OP-8EO, 4OP-9EO, 4OP-10EO, and activator 1 invert fully in 5 minutes.

The rate of inversion, or rate of viscosity build, was an important determinant of activity for anionic emulsion polymers used in upstream oil-recovery operations. Plots of torque versus time provided a way to evaluate the speed at which inversion took place. Field applications generally required that inversion occurred rapidly. The slope of the torque versus time curve in the early portion of the experiment was a good indicator of how rapidly inversion occurred. The torque typically levelled off to form a plateau region. Higher levels of torque in the plateau region indicated a higher emulsion viscosity.

The results of Examples 4a-4c demonstrated that blends of anionic emulsion polymers comprising a 4-octyloxyphenol ethoxylate surfactant (with an appropriate moles of EO) provided improved performance over the blends of anionic emulsion polymers comprising an equivalent amount of linear alcohol ethoxylates (Activators 2 and 3) in both fresh water and high TDS water. These data suggested that the surfactants can be substituted for linear alcohol ethoxylates (Activators 2 and 3) that are currently used as activator for anionic emulsion polymer formulations.

Example 4d: 8:2 Acrylamide/Acrylic Acid Emulsion Polymer—Inversion in High TDS (12.5%) Brine A standard 8:2 acrylamide/Acrylic acid emulsion co-polymer (emulsion polymer 7) without activating surfactant was used in this example. Anionic inverse emulsion polymers are used for friction reducing applications in oil and gas industries, more particularly during hydraulic fracturing to reduce pumping requirements. All evaluations with polymer 7 blends were done using torque method, and flow-loop experiments (described below) in high (12.3%) TDS brine. A series of three experiments was conducted.

Preparation of High (12.3%) TDS Brine:

The 12.3% TDS brine used in this example was formed by blending the components of Table 18. Brine was filtered through a WHATMAN 1 filter by suction filtration to remove any particulate.

TABLE 18

Ingredients of 12.3% TDS Brine

| Reagent | Amount (g) |
|---|---|
| NaCl | 91.83 |
| $CaCl_2$ $2H_2O$ | 21.60 |
| $MgCl_2$ $6H_2O$ | 7.71 |
| KCl | 0.908 |
| $SrCl_2$ $6H_2O$ | 1.179 |
| DI water | 876.77 |

Invertability Comparison of Polymer 7 Blends with 2.5 wt % Surfactants with 4 wt % Activator:

Emulsion polymer 7 was weighed into a 4 oz. bottle. Polymer 7 activator blends with indicated percent activator were made by blending activator into the emulsion while stirring. The resulting blends were stirred for one hour and allowed to stand for at least two hours before testing.

TABLE 19

Polymer 7 blends with activating surfactants at approximately 2.5-4%

| Activator | Weight Emulsion 7 (g) | Weight Activator(g) | Wt. Percent Activator (%) |
|---|---|---|---|
| 4OP-8EO | 78.097 | 2.011 | 2.51% |
| 4OP-9EO | 78.191 | 2.023 | 2.52% |
| 4OP-10EO | 78.009 | 1.997 | 2.50% |
| 4OP-11EO | 78.052 | 2.022 | 2.53% |
| 4OP-12EO | 78.075 | 2.028 | 2.53% |
| PR-9000 | 78.112 | 2.021 | 2.52% |
| PR-9000 | 76.813 | 3.213 | 4.01% |

Figure 26:
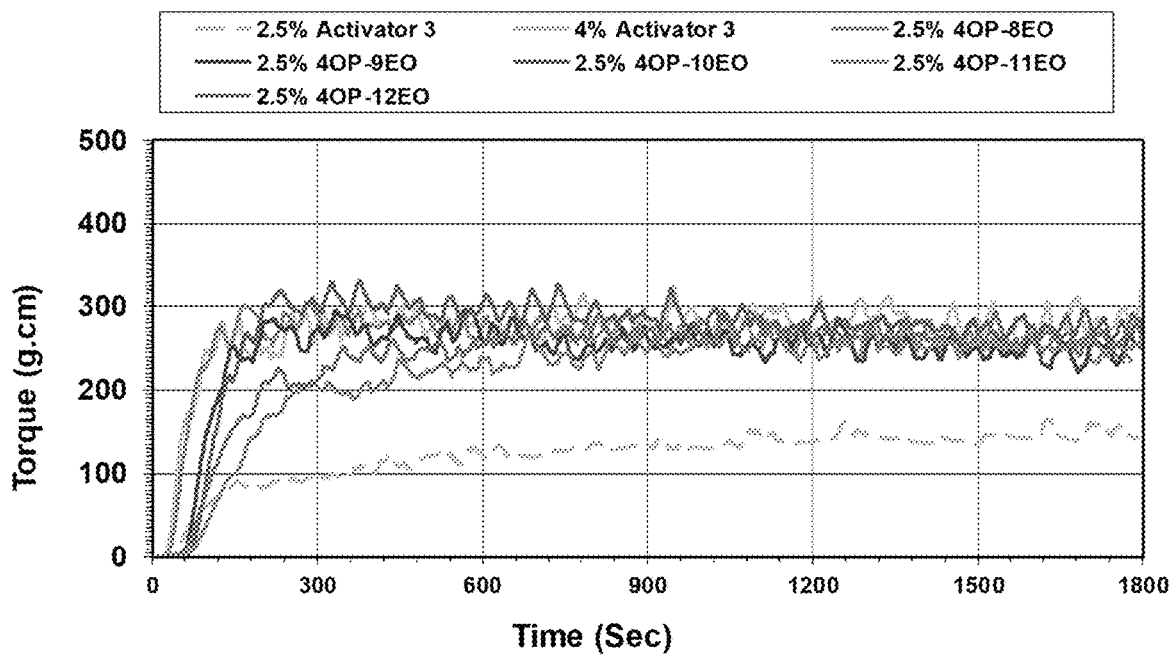
FIG. 26 is a graph of the torque versus time and shows the inversion torque profile (0.5% invert in 12.3% TDS brine) for polymer 7 with approximately 2.5-4% activating surfactant.

FIG. 26 depicts the inversion torque profile (0.5% invert in 12.3% TDS brine) for polymer 7 with approximately 2.5-4% activating surfactant. The rate of inversion for polymer 6 with 2.5% 4OP-8EO and 4% activator 3 were similar. The rate of inversion was faster for polymer 7 with all ethoxylated surfactants (4OP-nEO) than for polymer 7 with activator 3 at 2.5% (equivalent activator) concentrations.

Invertability Comparison of Polymer 7 Blends with 1.5-3 wt % 4OP-8EO and 4 wt % Activator 3 by Torque Measurements:

Emulsion polymer 7 was weighed into a 4 oz. bottle. Polymer 7 activator blends with indicated percent activator were made by blending activator into the emulsion while stirring. The resulting blends were stirred for one hour and allowed to stand for at least two hours before testing.

TABLE 17

Polymer 7 blends with activating surfactants

| Activator | Weight Emulsion 7 (g) | Weight Activator (g) | Wt. Percent Activator (%) |
|---|---|---|---|
| 4OP-8EO | 78.410 | 1.609 | 2.01% |
| 4OP-8EO | 78.107 | 2.003 | 2.50% |

TABLE 17-continued

Polymer 7 blends with activating surfactants

| Activator | Weight Emulsion 7 (g) | Weight Activator (g) | Wt. Percent Activator (%) |
|---|---|---|---|
| 4OP-8EO | 77.606 | 2.410 | 3.01% |
| 4OP-8EO | 78.812 | 1.211 | 1.51% |
| PR-9000 | 76.804 | 3.211 | 4.01% |

Figure 27:
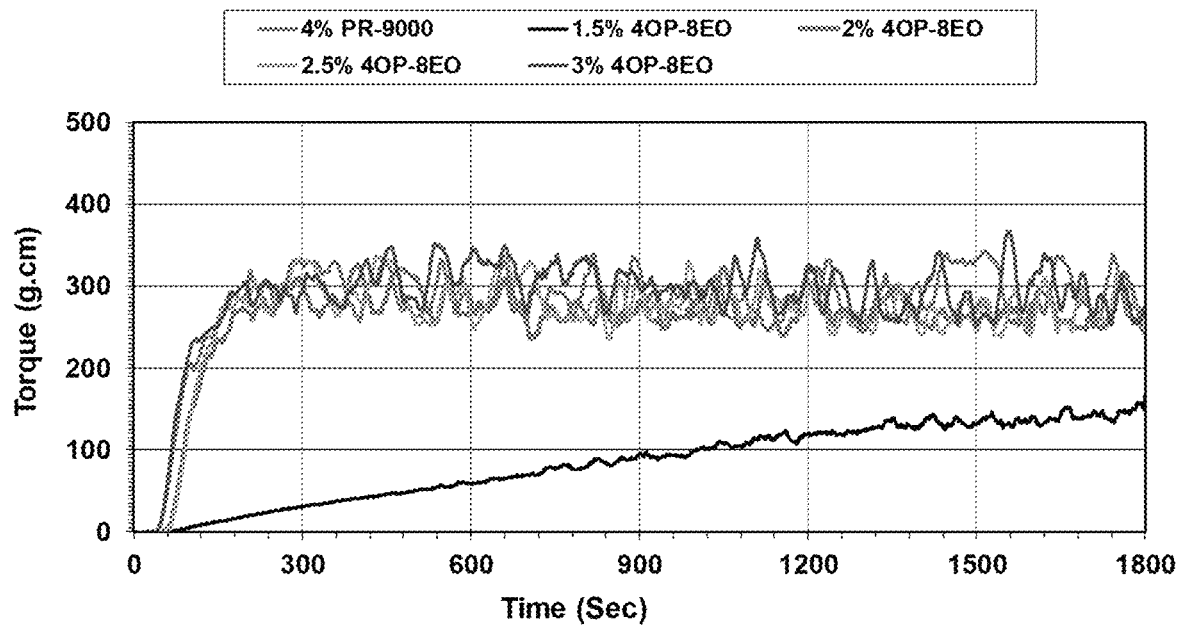
FIG. 27 is a graph of the torque versus time and shows an inversion torque profile (0.5% invert in 12.3% TDS brine) for polymer 7 with approximately 1.5-4% activators.

FIG. 27 depicts an inversion torque profile (0.5% invert in 12.3% TDS brine) for polymer 7 with approximately 1.5-4% activators. The rate of inversion for polymer 7 with 2.0%, 2.5%, and 3.0% 4OP-8EO and 4% activator 3 were comparable.

Figure 28:
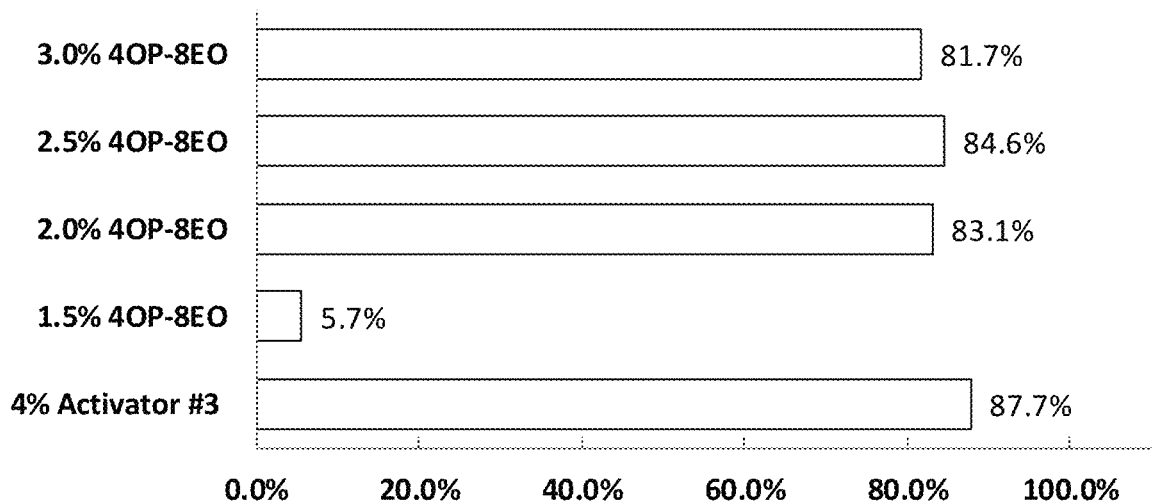
FIG. 28 shows a comparison of the 2 minute percent inversion of polymer 7 with activating surfactants.

FIG. 28 shows a comparison of the 2 minute percent inversion of polymer 7 with activating surfactants. The 2 minute percent inversion for polymer 7 with 4% activator 3 was greater than for the other polymers.

Figure 29:
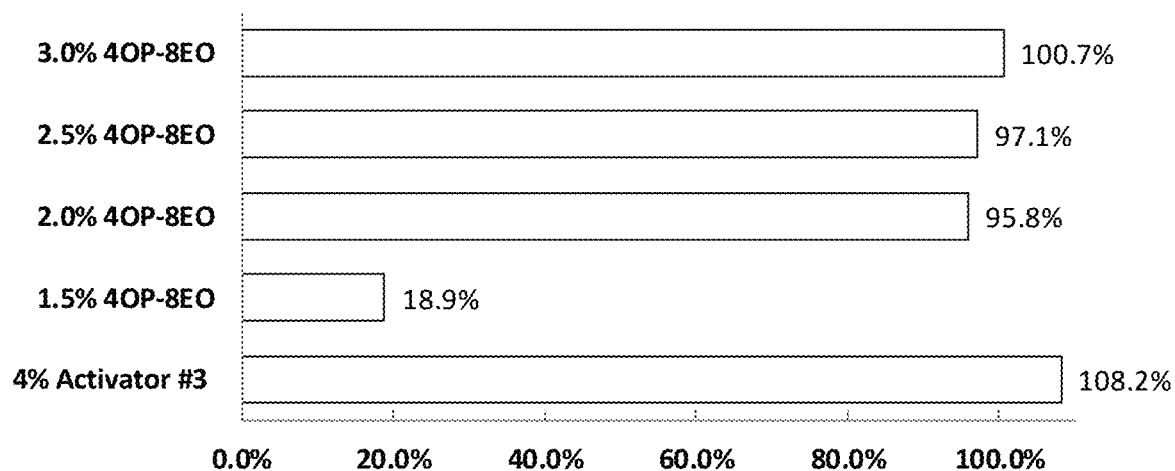
FIG. 29 shows a comparison of the 5 minute percent inversion of polymer 7 with activating surfactants.

FIG. 29 shows a comparison of the 5 minute percent inversion of polymer 7 with activating surfactants. The 5 minute percent inversion for polymer 7 with 4OP-7.2EO was greater than for the other polymers.

Friction Reduction Comparison of Polymer 7 Blends with 1.5-3 wt % 4OP-8EO and 4 wt % Activator 3 by Flow-Loop Experiments:

Flow loop tests were conducted on a recirculating flow loop through 0.5 inch pipe (ID=0.402 in) at 8 gpm (Reynold's number=6.3×10$^4$). A pressure drop was measured across a straight 4.83-foot section of pipe. Friction reduction was calculated according to Equation 1 below.

$$\text{Friction Reduction (\%)} = 100 \times \frac{P^1 - P^2}{P^1}$$

Where $P^1$ is the initial pressure drop and $P^2$ is the pressure drop after the addition of the friction reducer.

Figure 30:
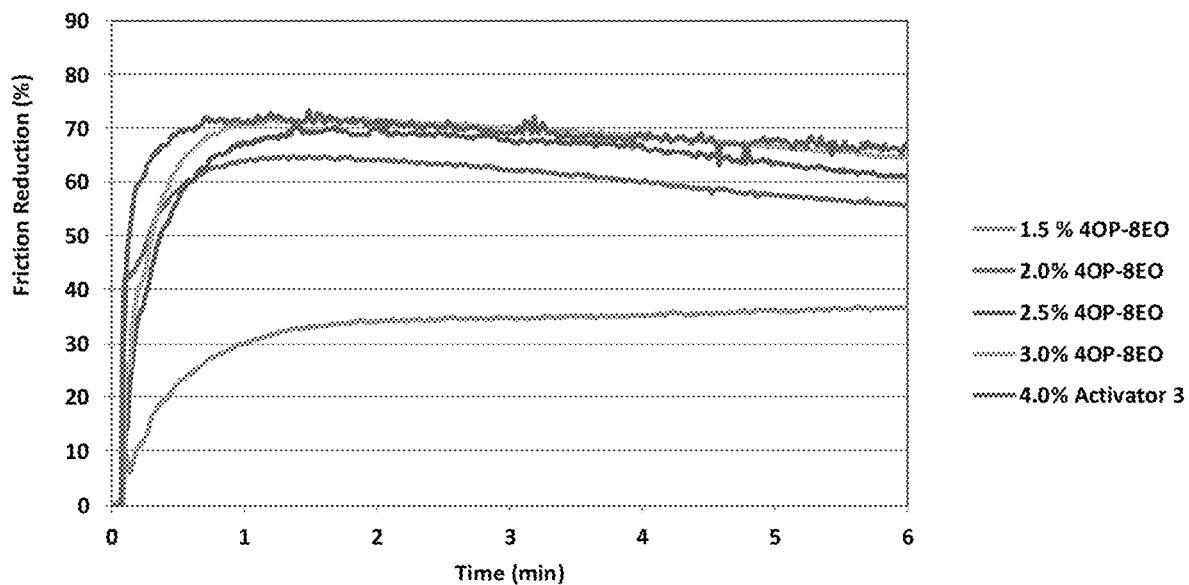
FIG. 30 is a graph of the percent friction reduction versus time and shows a comparison of the friction reduction properties of polymer 7 blends with 4% activator 3 and 1.5%, 2.0%, 2.5%, and 3.0% 4OP-8EO measured by flow loop tests in high TDS brine (13.4% TDS) at room temperature.

FIG. 30 shows a comparison of the friction reduction properties of polymer 7 blends with 4% activator 3 and 1.5%, 2.0%, 2.5%, and 3.0% 4OP-8EO measured by flow loop tests in high TDS brine (13.4% TDS) at room temperature.

Figure 31:
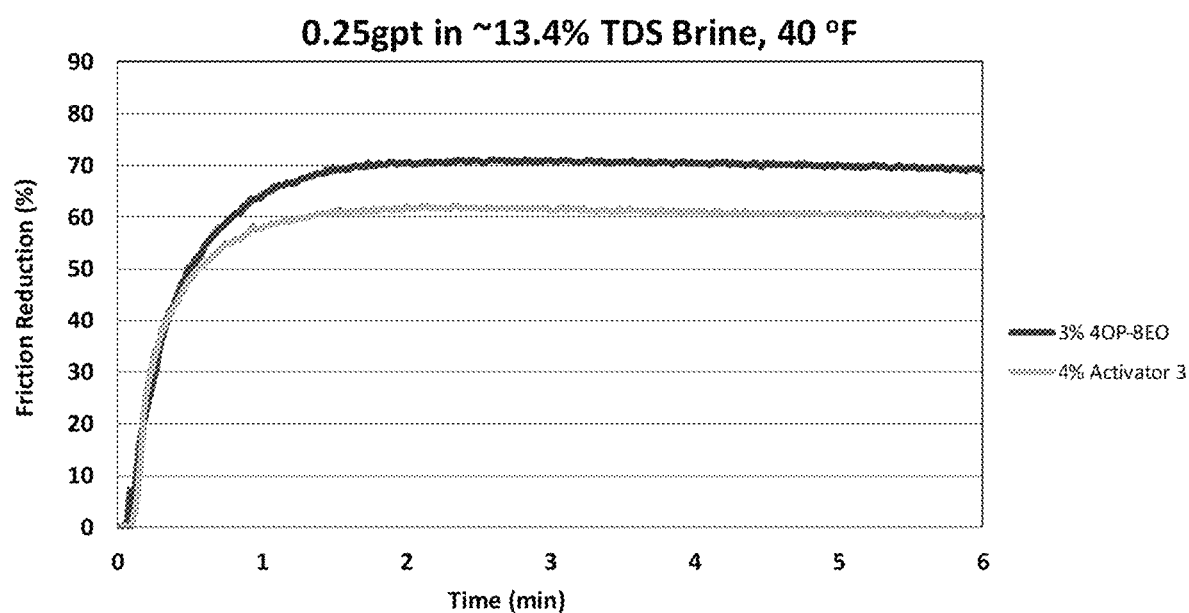
FIG. 31 is a graph of the percent friction reduction versus time and shows a comparison of the friction reduction properties of polymer 7 blend with 4% activator 3 and 3.0% 4OP-8EO measured by flow loop tests in high TDS brine (13.4% TDS) at 40° F.

FIG. 31 shows a comparison of the friction reduction properties of polymer 7 blend with 4% activator 3 and 3.0% 4OP-8EO measured by flow loop tests in high TDS brine (13.4% TDS) at 40° F.

In the flow loop experiments done at room temperature, polymer 7 blends with 4% Activator 3 and 3.0% 4OP-8EO showed similar friction reduction, i.e., about 70% friction reduction within one minute. In contrast, in the flow loop experiments done at lower temperature (40° F.), polymer 7 blends with 3.0% 4OP-8EO showed better friction reduction (about 70% within two minutes) compared to 4% Activator 3 (about 60% within two minutes).

The results of this example show that the inversion and friction reducing performance of polymer 7 blends with 4% SURFONIC TDA-9 was at least equivalent to that of polymer 7 blends with only 3% 4OP-8EO.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description and shown in the accompanying drawings shall be interpreted as illustrative and not in a limiting sense.

The invention claimed is:

1. A polymer composition comprising:
   a water-in-oil emulsion comprising an aqueous phase comprising water and a water-soluble or water-dispersible polymer, and an oil phase comprising an oil and an emulsifying agent; and
   an inversion surfactant having the structure of Formula 1:

$$\text{(1)}$$

[Structure of Formula 1 with substituents $R_3$, $R_5$, $R_6$, $R_9$, $R_{10}$, $R_{11}$, $XR_4$, and $(O)_n$]

wherein
$R_3$, $R_5$, $R_9$, and $R_{10}$ are independently hydrogen or $C_1$-$C_{22}$ alkyl;
$R_4$ is $C_4$-$C_{30}$ alkyl;
$R_6$ is H, alkyl, or aryl;
X is —O— or —$NR_8$;
$R_8$ is hydrogen or $C_1$-$C_4$ alkyl;
$R_{11}$ is hydrogen, alkyl, alkylaryl, or aryl; and
n is an integer from 1 to 20.

2. The polymer composition of claim 1, wherein the water-in-oil emulsion further comprises the inversion surfactant having the structure of Formula 1.

3. The polymer composition of claim 1, further comprising an aqueous solution containing the inversion surfactant having the structure of Formula 1.

4. The polymer composition of claim 1, wherein $R_4$ is $C_4$-$C_{16}$ alkyl.

5. The polymer composition of claim 4, wherein X is —O—.

6. The polymer composition of claim 5, wherein n is an integer from 4 to 10.

7. The polymer composition of claim 6, wherein $R_3$, $R_5$, $R_9$, and $R_{10}$ are independently hydrogen or methyl.

8. The polymer composition of claim 7, wherein $R_3$, $R_5$, $R_9$, and $R_{10}$ are hydrogen.

9. The polymer composition of claim 6, wherein $R_6$ is hydrogen or methyl.

10. The polymer composition of claim 6, wherein $R_{11}$ is hydrogen or alkyl.

11. The polymer composition of claim 1, wherein $R_4$ is $C_8$-$C_{12}$ alkyl.

12. The polymer composition of claim 1, wherein the water-soluble or water-dispersible polymer comprises a polyacrylamide, a polyacrylic acid, or a combination thereof.

13. The polymer composition of claim 1, wherein the inversion surfactant having the structure of Formula 1 has a concentration of from about 0.1 wt. % to about 10 wt. % based on the total weight of the emulsion.

14. The polymer composition of claim 1, wherein the polymer composition further comprises an ethoxylated $C_{10}$-$C_{16}$ alcohol; a $C_{12}$-$C_{13}$ primary alcohol of linear and monomethyl branched alcohol having on average 9 moles ethylene oxide; an ethoxylate of a saturated $C_{12-15}$ alcohol; an ethoxylated $C_{12-14}$ alcohol; an ethoxylated primary branched saturated $C_{13}$ alcohol; an ethoxylated $C_{10}$ Guerbet alcohol; an ethoxylated saturated iso-$C_{13}$ alcohol; a saturated, predominantly unbranched $C_{13-15}$ oxo alcohol having 11 ethylene oxide groups; a secondary alcohol ethoxylate; a nonionic, alkoxylated alcohol; a polyoxyethylene (9) synthetic primary $C_{13}/C_{15}$ alcohol; an isotridecyl alcohol ethoxylated with an average of 9 moles ethylene oxide; an ethoxylated linear primary $C_{12-14}$ alcohol; an ethoxylated nonylphenol; tert-octylphenoxypoly(ethoxyethanol); a tridecyl ether phosphate; a polyoxyethylene (5) soyaallylamine; a polyethylene glycol (PEG) 400 monooleate; a PEG 600 monooleate; aPEG-25 castor oil; a PEG-30 castor oil; a PEG-40 castor oil; an aliphatic phosphate ester with 10 moles EO; an aliphatic phosphate ester with 6 moles EO; an oleic acid monoethanol amide with 14 moles ethylene oxide; a soyamine ethoxylate; or a combination thereof.

15. A method of dissolving the water-soluble or water-dispersible polymer of the polymer composition of claim 1 comprising contacting the water-in-oil emulsion with the inversion surfactant having the structure of Formula 1.

16. The method of claim 15, wherein the water-in-oil emulsion further comprises the inversion surfactant having the structure of Formula 1 and the water-in-oil emulsion is contacted with an aqueous solution.

17. The method of claim 15, wherein the water-in-oil emulsion is contacted with an aqueous solution comprising the inversion surfactant having the structure of Formula 1.

18. The method of claim 15, wherein the inversion surfactant is activated by contacting the inversion surfactant with an inversion aid and the inversion aid comprises glycol, a polypropylene glycol, polyglycerol, urea, sorbitol, sucrose, glycerol, a polyglycerol, a phosphate, choline chlorine, guanidine, dioctyl-sulfosuccinate, malic acid, lactic acid, N-(phosphonomethyl)glycine, 2-phosphonopropanoic acid, 3-phosphonopropanoic acid, 4-phosphonobutanoic acid, a phosphinosuccinic oligomer, a polyethylene glycol, urea, sorbitol, sucrose, glycerol, a phosphate, choline chlorine, or a combination thereof.

19. A compound having the structure of Formula 2:

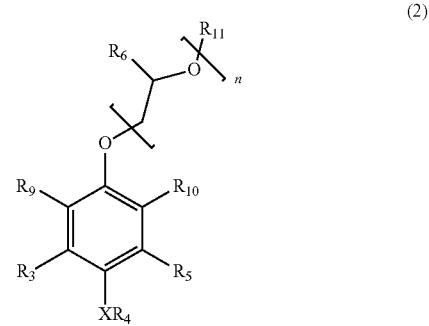

(2)

wherein
$R_3$, $R_5$, $R_9$, and $R_{10}$ are independently hydrogen or $C_1$-$C_{22}$ alkyl;
$R_4$ is $C_4$-$C_{30}$ branched alkyl;
$R_6$ is H, alkyl, or aryl;
X is —O— or —$NR_8$;
$R_8$ is hydrogen or $C_1$-$C_4$ alkyl;
$R_{11}$ is hydrogen, alkyl, alkylaryl, or aryl; and
n is an integer from 1 to 20.

20. The compound of claim 19, wherein
$R_3$, $R_5$, $R_9$, $R_{10}$, and $R_{11}$ are hydrogen;
$R_4$ is $C_8$-$C_{16}$ branched alkyl;
X is —O—; and
n is an integer from 1 to 20.

* * * * *